(12) United States Patent
Ince et al.

(10) Patent No.: US 8,912,156 B1
(45) Date of Patent: Dec. 16, 2014

(54) MARKERS FOR AND METHODS OF TARGETING TUMOR STEM CELLS

(75) Inventors: Tan A. Ince, Miami, FL (US); Tong Ihn Lee, Somerville, MA (US); Richard A. Young, Weston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 13/365,073

(22) Filed: Feb. 2, 2012

Related U.S. Application Data

(60) Provisional application No. 61/439,743, filed on Feb. 4, 2011.

(51) Int. Cl.
*A61K 48/00* (2006.01)
*C07H 21/02* (2006.01)
*C07H 21/04* (2006.01)

(52) U.S. Cl.
USPC ............................ 514/44; 536/23.1; 536/24.5

(58) Field of Classification Search
CPC ........................ C12N 2310/321; C12N 15/113
See application file for complete search history.

(56) References Cited

U.S. PATENT DOCUMENTS

| | | | |
|---|---|---|---|
| 6,984,522 B2 | 1/2006 | Clarke et al. | |
| 7,115,360 B2 | 10/2006 | Clarke et al. | |
| 7,713,710 B2 | 5/2010 | Clarke et al. | |
| 7,754,206 B2 | 7/2010 | Clarke et al. | |
| 7,850,961 B2 | 12/2010 | Clarke et al. | |
| 2004/0072770 A1* | 4/2004 | Besterman et al. | 514/44 |
| 2010/0233693 A1 | 9/2010 | Kopf-Sill et al. | |

OTHER PUBLICATIONS

Karamboulas et al. (journal of Cell Science, 119 (20), 4305-4314, 2006).*
Dequiedt, et al., "New Role for hPar-1 Kinases EMK and C-TAK1 in Regulating Localization and Activity of Class IIa Histone Deacetylases," Molecular and Cellular Biology, 26(19): 7086-7102 (2006).
Young, Richard A., Abstract "*Epigenomic Mapping in Human Tumor Stem Cells*" National Cancer Institute Grant No. 1 R01 CA146445-01 (Funding Start Date Aug. 21, 2009).
Bao, et al.,"Glioma stem cells promote radioresistance by preferential activation of the DNA damage response", *Nature*, 444: 756-760 (2006).
Botrugno, et al., "Histone deacetylase inhibitors as a new weapon in the arsenal of differentiation therapies of cancer", *Cancer Letters*, 280: 134-144 (2009).
Carew, et al., Histone deacetylase inhibitors: Mechanisms of cell death and promise in combination cancer therapy, *Cancer Letters*, 269: 7-17 (2008).
Chang, et al., "Histone Deacetylases 5 and 9 Govern Responsiveness of the Heart to a Subset of Stress Signals and Play Redundant Roles in Heart Development", *Molecular and Cellular Biology*, 24(19): 8467-8476 (2004).

Charafe-Jauffret, et al., Breast Cancer Cell Lines Contain Functional Cancer Stem Cells with Metastatic Capacity and a Distinct Molecular Signature, *Cancer Research*, 69: 1302-1313 (2009).
Dokmanovic, et al., "Histone deacetylase inhibitors selectively suppress expression of HDAC7", *Molecular Cancer Therapeutics*, 6: 2525-2534 (2007).
Duong, et al., "Specific Activity of Class II Histone Deacetylases in Human Breast Cancer Cells", *Molecular Cancer Research*, 6: 1908-1919 (2008).
Eyler, et al., "Survival of the Fittest: Cancer Stem Cells in Therapeutic Resistance and Angiogenesis", *Journal of Clinical Oncology*, 26(17): 2839-2845 (2008).
Gupta, et al., "Identification of Selective Inhibitors of Cancer Stem Cells by High-Throughput Screening", *Cell*, 138: 645-659 (2009).
Iacobuzio-Donahue, Christine A., "Epigenetic Changes in Cancer", *Annual Review of Pathology:Mechanisms of Disease*, 4: 229-249 (2009).
Ince, et al., "Transformation of Different Human Breast Epithelial Cell Types Leads to Distinct Tumor Phenotypes", *Cancer Cell*, 12: 160-170 (2007).
Keshet, et al., "Transformation of Different Human Breast Epithelial Cell Types Leads to Distinct Tumor Phenotypes", *Nature Genetics*, 38(2): 149-153 (2006).
Krivtsov, et al., "MLL translocations, histone modifications and leukaemia stem-cell development", *Cancer*, 7: 823-833 (2007).
Lawson, et al., "Cancer stem cells in breast cancer and metastasis", *Breast Cancer Research & Treatment*, 118: 241-254 (2009).
Liu, et al., "The Prognostic Role of a Gene Signature from Tumorigenic Breast-Cancer Cells", *The New England Journal of Medicine*, 256(3): 217-226 (2007).
Shankar, et al., "Histone Deacetylase Inhibitors: Mechanisms and Clinical Significance in Cancer", *Advances in Experimental Medicine and Biology*, 615: 261-298 (2007).
Ting, et al., "The cancer epigenome—components and functional correlates", *Genes & Development*, 20: 3215-3231 (2006).
Yoo, et al., "Epigenetic therapy of cancer: past, present and future", *Drug Discovery*, 5: 37-50 (2006).
Zhang, et al., "Class II Histone Deacetylases Act as Signal-Responsive Repressors of Cardiac Hypertrophy", *Cell*, 110: 479-488 (2002).

* cited by examiner

*Primary Examiner* — Amy Bowman
(74) *Attorney, Agent, or Firm* — Lisa M. Warren, Esq.; David A. Fazzolare, Esq.; Morse, Barnes-Brown & Pendleton P.C.

(57) ABSTRACT

The invention provides methods of targeting tumor stem cells that comprise inhibiting the level and/or activity of HDAC1, HDAC7 and phosphorylated HDAC7. The invention further provides methods for identifying tumor stem cells comprising detecting increased levels and/or activity of HDAC1, HDAC7 and phosphorylated HDAC7. Further provided are kits and articles of manufacture comprising inhibitors of the level and/or activity of HDAC1, HDAC7 and phosphorylated HDAC7. Methods for screening for inhibitors of the level and/or activity of HDAC1, HDAC7 and phosphorylated HDAC7 are also provided.

18 Claims, 6 Drawing Sheets

Figure 2
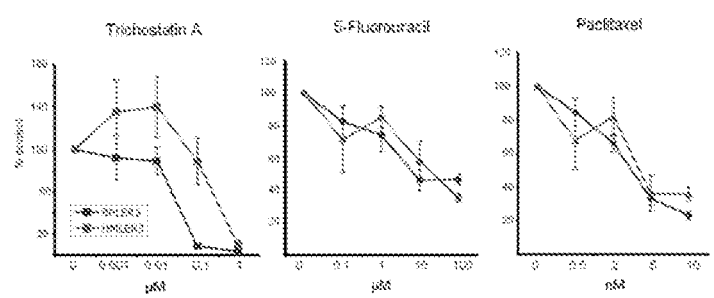
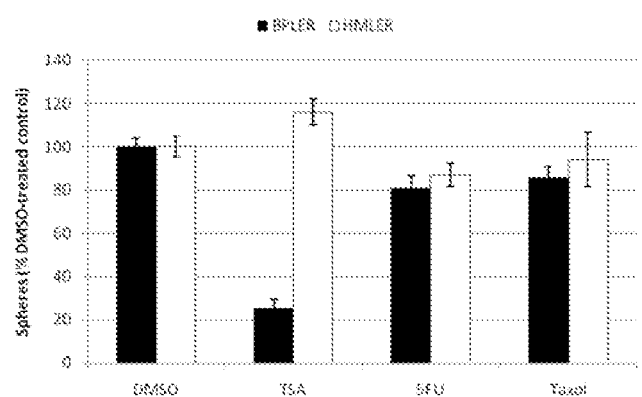

Figure 4
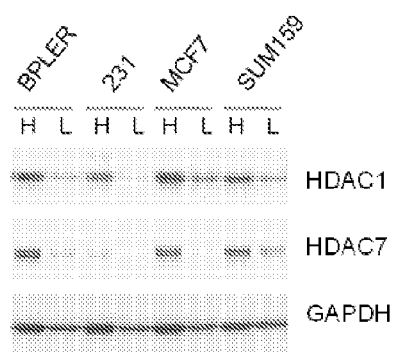
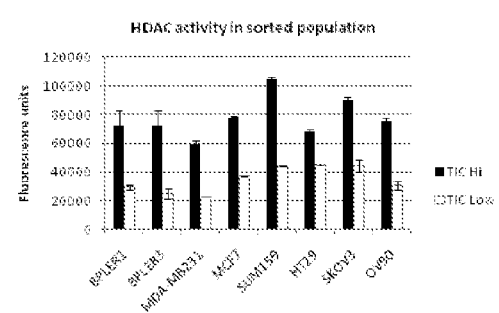

MARKERS FOR AND METHODS OF TARGETING TUMOR STEM CELLS

CROSS-REFERENCE TO RELATED APPLICATION

This application claims the benefit of, and priority to, U.S. Provisional Application No. 61/439,743 filed Feb. 4, 2011, the entire contents of which is incorporated herein by reference.

GOVERNMENT SUPPORT

The invention was supported, in whole or in part, by grant NIH-IR01CA146445-01 from the National Cancer Institute. The U.S. Government has certain rights in the invention.

BACKGROUND OF THE INVENTION

Tumor stem cells (TSCs) are the only subpopulation of a heterogeneous mixture of tumor cells that have the capacity to regenerate tumors in vivo. Tumor stem cells are also are characterized by their capacity for self-renewal, and differentiation into the myriad other types of cells typically found in malignant tumors. Like ordinary cells, the TSC phenotype is controlled by a unique gene expression program. However, the regulatory mechanisms that control TSC gene expression leading to malignant tumor initiation and proliferation are unclear. A better understanding of the regulatory mechanisms that govern TSC gene expression and contribute to the TSC identity would be of considerable scientific and practical interest.

SUMMARY OF THE INVENTION

The invention relates at least in part to the discovery that tumor stem cells exhibit increased levels and/or activity of HDAC1 and/or HDAC7 and/or phosphorylated HDAC7 protein.

In some aspects, the invention provides a method for inhibiting the proliferation of one or more tumor stem cells that includes contacting said one or more cells with an effective amount of at least one inhibitor of HDAC1 and/or HDAC7 and/or phosphorylated HDAC7.

In some embodiments, the inhibitor of HDAC1 and/or HDAC7 and/or phosphorylated HDAC7 specifically inhibits the level and/or activity of HDAC1 and/or HDAC7 and/or phosphorylated HDAC7 protein.

In some embodiments, the inhibitor of HDAC7 and/or phosphorylated HDAC7 specifically inhibits the level and/or activity of EMK and/or CTAK-1 and/or CaMK protein kinase.

In some embodiments, the inhibitor of HDAC7 and/or phosphorylated HDAC7 specifically increases the level and/or activity of PP2A phosphatase.

In some embodiments, the inhibitor of HDAC1 and/or HDAC7 and/or phosphorylated HDAC7 is an antisense nucleic acid, an oligopeptide, an aptamer, a ribozyme, a small molecule, and an antibody or a fragment thereof.

In some embodiments, the one or more cells is a breast tumor stem cell, ovarian tumor stem cell, colon tumor stem cell, brain tumor stem cell, pancreatic tumor stem cell, prostate tumor stem cell, or a lung tumor stem cell.

In some aspects, the present invention provides a method for inhibiting the proliferation of, or eliminating, one or more tumor stem cells that includes contacting said cell with an effective amount of both at least one HDAC1 inhibitor and at least one HDAC7 inhibitor. Inhibiting the proliferation of, or eliminating, one or more tumor stem cells causes a result selected from the group consisting of transforming the one or more tumor stem cells into a non-stem tumor cell e.g., any other cancerous cell that does not contain tumor stem cells, reducing the growth rate of a tumor containing the tumor stem cells, reducing the overall growth of the tumor containing the tumor stem cells, reducing the amount of tumor stem cells present in the tumor containing the tumor stem cells, reducing the accumulation of tumor stem cells in the tumor containing the tumor stem cells, and reducing the capacity for the tumor stem cells to generate new tumor stem cells or new tumor cells. In some embodiments, inhibiting the proliferation of the one or more tumor stem cells includes inhibiting a significant fraction of the tumor stem cells present in a tumor containing the tumor stem cells.

In some embodiments, the HDAC1 and HDAC7 inhibitors specifically inhibit the level and/or activity of both HDAC1 and HDAC7 protein. The HDAC1 inhibitor and the HDAC7 inhibitor may include antisense nucleic acids, oligopeptides, aptamer, ribozymes, small molecules, and antibodies or a fragments thereof.

In some embodiments, the HDAC7 inhibitor specifically inhibits the level and/or activity of EMK and/or CTAK-1 and/or CaMK protein kinase.

In some embodiments, the HDAC7 inhibitor specifically increases the level and/or activity of PP2A and/or myosin phosphatase.

In some embodiments, one or more cells includes breast tumor stem cells, ovarian tumor stem cells, colon tumor stem cells, brain tumor stem cells, pancreatic tumor stem cells, prostate tumor stem cells, or a lung tumor stem cells.

In some aspects, the present invention provides a method for treating a tumor that includes administering to an individual in need thereof an effective amount of an agent which specifically inhibits the level and/or activity of HDAC1 and/or HDAC7 protein. The method for treating a tumor can be useful for treating solid tumors e.g., breast tumors, ovarian tumors, colon tumors, brain tumors, pancreatic tumors, prostate tumors, or lung tumors, or for treating a hematological tumor e.g., leukemias, myelomas, or lymphomas, etc.

In some embodiments, the agent specifically inhibits the level and/or activity of a phosphorylated HDAC7 protein. In some embodiments, a serine amino acid residue of the HDAC7 protein is phosphorylated. In some embodiments, serine-155 is phosphorylated. In some embodiments, serine-318 is phosphorylated. In some embodiments, the phosphorylated serine residue includes one of serine-155, serine-178, serine-318, serine 344 or serine-479, and combinations thereof.

In some embodiments, the agent specifically inhibits the level and/or activity of EMK and/or CTAK-1 and/or CaMK protein kinase.

In some embodiments, the agent specifically increases the level and/or activity of PP2A and/or myosin phosphatase.

The agent may include an antisense oligonucleotide, a ribozyme, an siRNA molecule, an aptamer, an RNA hairpin, and an antibody or a fragment thereof. In some embodiments, the agent is administered with a pharmaceutically acceptable carrier. In some embodiments, the agent is co-administered with at least one additional chemotherapeutic agent.

In some embodiments, the agent is an interfering RNA targeted to HDAC1 and/or HDAC7 mRNA in the individual, which interferes with HDAC1 and/or HDAC7 expression within the individual. Examples of suitable interfering RNA include siRNA and RNA hairpins.

In some embodiments, the agent is an oligonucleotide having a nucleotide sequence that is complementary to HDAC1 and/or HDAC7 mRNA within the individual. In some embodiments, the oligonucleotide is within the range of about 5 to about 50 nucleotides in length.

In some aspects, the present invention provides a method for treating cancer that includes administering to an individual in need thereof an effective amount of an agent which specifically inhibits the level and/or activity of HDAC1 and/or HDAC7. The cancer is one in which one or more cancerous cells produces increased levels of HDAC1 and/or HDAC7 and/or phosphorylated HDAC7 protein. In some embodiments, the one or more cancerous cells produce increased levels of both HDAC1 and HDAC7 protein. In some embodiments, the one or more cancerous cells produce increased levels of both HDAC1 and phosphorylated HDAC7 protein.

The one or more cancerous cells include tumor stem cells. In some embodiments, the cancer includes breast cancer, ovarian cancer, colon cancer, brain cancer, pancreatic cancer, prostate cancer, lung cancer, or melanoma. In some embodiments, the cancer includes leukemia, myeloma, or lymphoma.

In some embodiments, the agent reduces a significant fraction of the tumor stem cells in the cancer. In some embodiments, the agent specifically inhibits the level and/or activity of HDAC1 and/or HDAC7 in a tumor stem cell. In some embodiments, the agent specifically inhibits the level and/or activity of phosphorylated HDAC7 in a tumor stem cell. In some embodiments, the agent specifically inhibits the level and/or activity of HDAC7 phosphorylated at a serine amino acid residue e.g., such as serine-155 or serine-318, for example. In some embodiments, the phosphorylated serine is one of serine-155, serine-178, serine-318, serine-344 or serine-479, and combinations thereof.

In some embodiments, the agent is an agent which downregulates HDAC1 and/or HDAC7 gene expression, inhibits HDAC1 and/or HDAC7 translation, inhibits HDAC1 and/or HDAC7 and/or phosphorylated HDAC7 protein activity, and/or reduces the level of HDAC1 and/or HDAC7 and/or phosphorylated HDAC7 protein. In some embodiments, the agent downregulates both HDAC1 and HDAC7 gene expression, inhibits both HDAC1 and HDAC7 translation, inhibits both HDAC1 and HDAC7 protein activity, and/or reduces the level of both HDAC1 and HDAC7 protein.

The agent can be used to inhibit the proliferation of, or to eliminate, tumor stem cells.

The HDAC1 activity inhibited may include one or more of the following activities: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA, and combinations thereof.

The HDAC7 activity inhibited may include one or more of the following activities: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA; reduction of covalent bonding between a serine amino acid residue on HDAC7 and a phosphoryl group; reduction in the amount of phosphorylated serine amino acid residues on HDAC7; dephosphorylation of existing phosphorylated serine amino acid residues on HDAC7; prevention of subsequent phosphorylation of serine amino acid residues on HDAC7 whether by direct inhibition of protein kinases or direct activation of protein phosphatases, or by blocking the phosphorylation site by a binding molecule that directly binds to HDAC7; and combinations thereof.

In some embodiments, the HDAC7 is phosphorylated at a serine amino acid residue. In some embodiments, the serine phoshphorylated includes serine-155, serine-178, serine-318, serine-344 or serine-479, and combinations thereof.

In some embodiments, the agent is an agent that inhibits transcription of HDAC1 and/or HDAC7 mRNA, degrades HDAC1 and/or HDAC7 mRNA, inhibits translation of HDAC1 and/or HDAC7 mRNA, and combinations thereof. In some embodiments, the agent is an agent that inhibits transcription of both HDAC1 and HDAC7 mRNA, degrades both HDAC1 and HDAC7 mRNA, inhibits translation of both HDAC1 and HDAC7 mRNA, and combinations thereof.

In some embodiments, the agent that inhibits transcription of HDAC1 and/or HDAC7 mRNA is an interfering RNA (RNAi). In some embodiments, the agent that inhibits transcription of both HDAC1 and HDAC7 mRNA is an interfering RNA (RNAi).

In some embodiments, the agent that degrades HDAC1 and/or HDAC7 mRNA is an interfering RNA (RNAi). In some embodiments, the agent that degrades both HDAC1 and HDAC7 mRNA is an interfering RNA (RNAi).

In some embodiments, the agent that inhibits translation of HDAC1 and/or HDAC7 mRNA, and both HDAC1 and HDAC7 mRNA comprises an antisense nucleic acid, an oligopeptide, a ribozyme, and combinations thereof.

In some aspects, the present invention provides a method for generating a tumor stem cell that includes overexpressing in a cell the level and/or activity of both HDAC1 and HDAC7 protein, wherein overexpression of HDAC1 and HDAC7 protein within the cell transforms the cell into a tumor stem cell.

In some aspects, the present invention provides a method for generating a tumor stem cell that includes overexpressing in a cell the level and/or activity of both HDAC1 and phosphorylated HDAC7 protein, wherein overexpression of HDAC1 and phosphorylated HDAC7 protein within the cell transforms the cell into a tumor stem cell.

In some aspects, the present invention provides an article of manufacture comprising, packaged together, a specific inhibitor of HDAC1 and/or HDAC7 and/or phosphorylated HDAC7 or a pharmaceutical composition thereof comprising a pharmaceutically acceptable carrier; and a label stating that the inhibitor or pharmaceutical composition is indicated for treating patients having a tumor comprising tumor stem cells that exhibit increased HDAC1 and/or HDAC7 and/or phosphorylated HDAC7 protein levels.

In some aspects, the present invention provides a method for detecting tumor stem cells comprising detecting the presence of increased levels of HDAC1 and/or HDAC7 and/or phosphorylated HDAC7 protein in a sample containing cells. In some embodiments, detecting tumor stem cells includes detecting the presence of increased levels of both HDAC1 and HDAC7 protein in a sample containing cells. In some embodiments, detecting tumor stem cells includes detecting the presence of increased levels of both HDAC1 and phosphorylated HDAC7 protein in a sample containing cells.

In some embodiments, the increased level of HDAC1 and/or HDAC7 and/or phosphorylated HDAC& protein in the sample compared to standard levels of HDAC1 and/or HDAC7 and/or phosphorylated HDAC7 protein indicates that the sample contains tumor stem cells.

In some embodiments, the cells include one of breast cells, ovarian cells, colon cells, brain cells, pancreatic cells, lung cells, or prostate cells. In some embodiments, the sample is a cell sample obtained from a human subject.

In some aspects, the present invention provides a method of identifying a tumor stem cell that includes measuring in a cell the level of HDAC1 and/or HDAC7 protein and comparing the result of the measurement obtained with that of a control measurement, wherein an increased level of HDAC1 and/or HDAC7 protein indicates that the cell is a tumor stem cell. In some embodiments, the cell is a breast cell, ovarian cell, colon cell, brain cell, pancreatic cell, lung cell, or prostate cell. In some embodiments, the cell is a cell obtained from a human subject.

In some aspects, the present invention provides a method for identifying a compound that inhibits tumor stem cell proliferation in vitro comprising the steps of: (a) contacting HDAC1 and/or HDAC7 with a test substance; (b) measuring the activity of HDAC1 and/or HDAC7; and (c) determining whether the test substance inhibits the activity of HDAC1 and/or HDAC7. In some embodiments, the test compound is a small molecule. In some embodiments, the test compound is selected from the group consisting of an antisense oligonucleotide, an oligopeptide, a ribozyme, an siRNA, an aptamer, and an antibody or a fragment thereof.

In some aspects, the present invention provides a method of identifying a candidate agent that inhibits HDAC1 and/or HDAC7 expression or activity, the method including: a) expressing HDAC1 and/or HDAC7 protein in a cell population; b) contacting said population with said candidate agent; and c) measuring the level of expression or activity of HDAC1 and or HDAC7; wherein a decrease in expression or activity of the HDAC1 and/or HDAC7 protein relative to a control cell population not exposed to said candidate agent is indicative of HDAC1 and/or HDAC7 inhibitory activity of said candidate agent.

In some embodiments, the candidate agent is a small molecule. In some embodiments, the candidate agent is selected from the group consisting of an antisense oligonucleotide, an oligopeptide, a ribozyme, an siRNA, a ribozyme, an aptamer, and an antibody or a fragment thereof.

In some aspects, the present invention provides a method of identifying compounds useful for the treatment and/or prevention of solid tumors and/or hematological tumors comprising selecting compounds that reduce HDAC1 and/or HDAC7 protein or activity in a cell, wherein the selected compounds that reduce HDAC1 and/or HDAC7 protein or activity in the cell are useful for the treatment and/or prevention of solid tumors and/or hematological tumors.

In some embodiments, the selecting step comprises contacting the test compound with HDAC1 and/or HDAC7 protein or with a cell exhibiting increased levels and/or activity of HDAC1 and/or HDAC7 protein. In some embodiments, selecting step comprises identifying compounds that inhibit HDAC1 and/or HDAC7 activity. In some embodiments, the selecting step comprises identifying compounds that reduce the expression of HDAC1 and/or HDAC7 in cells. In some embodiments, the compounds that reduce the expression of HDAC1 and/or HDAC7 in cells reduce the amount of HDAC1 and/or HDAC7 encoding transcripts in cells. In some embodiments, the compounds that reduce the amount of HDAC1 and/or HDAC7 encoding transcripts in the cells are small interfering nucleic acids that induce RNA interference e.g., small RNA hairpins, for example.

In some embodiments, the compounds that reduce the expression of HDAC1 and/or HDAC7 in cells reduce the amount of translation of HDAC1 and/or HDAC7 encoding transcripts in the cells. In some embodiments, the compounds that reduce the expression of HDAC1 and/or HDAC7 in cells are antisense nucleic acids.

In some embodiments, the contacting step comprises identifying compounds that inhibit the enzymatic activity of HDAC1 and/or HDAC7.

In some embodiments, the compounds that inhibit the enzymatic activity of HDAC1 can be identified according to their ability to perform one or more of the following activities: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA, and combinations thereof.

In some embodiments, the compounds that inhibit the enzymatic activity of HDAC7 can be identified according to their ability to perform one or more of the following activities: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA; reduction of covalent bonding between a serine amino acid residue on HDAC7 and a phosphoryl group; reduction in the amount of phosphorylated serine amino acid residues on HDAC7; dephosphorylation of existing phosphorylated serine amino acid residues on HDAC7; prevention of subsequent phosphorylation of serine amino acid residues on HDAC7 whether by direct inhibition of protein kinases or direct activation of protein phosphatases, or by blocking the phosphorylation site by a binding molecule that directly binds to HDAC7; and combinations thereof.

In some embodiments, the HDAC7 protein is phosphorylated. In some embodiments, the HDAC7 protein is phosphorylated at a serine amino acid residue. In some embodiments, the serine residue that is phosphorylated is serine-155. In some embodiments, the serine residue that is phosphorylated is serine-318. In some embodiments, the phosphorylated serine residue includes serine-155, serine-178, serine-318, serine-344 or serine-479.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009). Non-limiting information regarding genes and genetic disorders is found in McKusick, V. A.: Mendelian inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2. HDAC inhibitor TSA specifically targets tumor stem cells. A) Graph showing results of inhibition of cell proliferation of TSC-like BPLER cell vs. non-STC-like HMLER cells by the HDAC inhibitor Trichostatin A (TSA). Graph further shows that HDAC inhibitor TSA inhibition of cell proliferation as compared to chemotherapeutics paclitaxel (microtubule inhibitor), and 5-fluorouracil (DNA synthesis inhibitor). B) Chart showing inhibition of tumor sphere formation of TSC-like BPLER cell vs. non-STC-like HMLER cells by HDAC inhibitor Trichostatin A (TSA).

FIG. 4. HDAC1 and HDAC7 are highly expressed in tumor stem cells. A) Western blot showing that extracts from FACS enriched CD44-high/CD166-high subpopulation (H) of TSCs have higher levels of HDAC1 and HDAC7 protein than that of CD44-low/CD166-low (L) in BPLER, MDA-MB-231, MCF-7, and SUM-159 tumor cells. GADPH expression was used as loading control. B) Chart showing results of HDAC activity assay. Chart shows higher global HDAC activity in TSC-enriched subpopulation breast, ovarian and colon tumor cells lines.

DETAILED DESCRIPTION OF THE INVENTION

Figure 1:
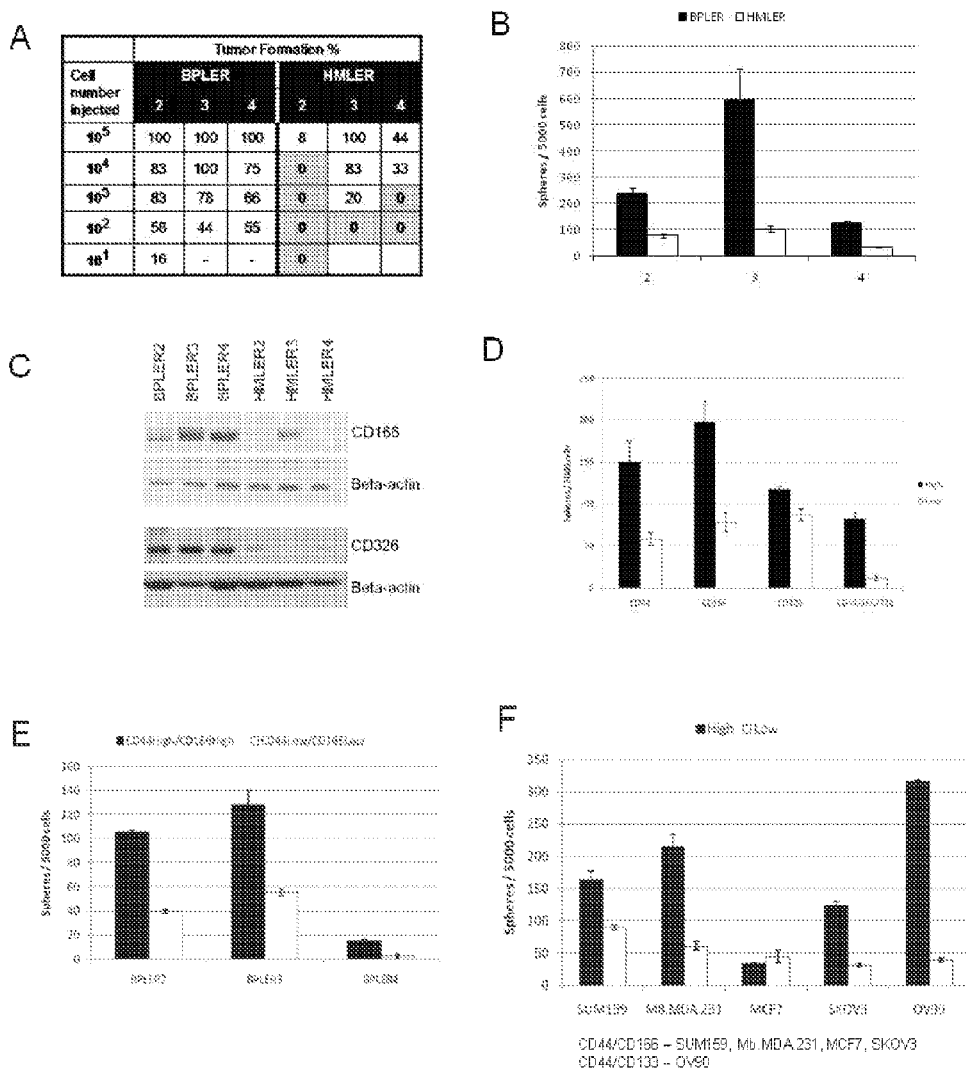
FIG. 1. Subpopulations of isogenic tumor cells have stem and non-stem properties. A) Table of tumor formation efficiency of BPLER and HMLER cells compared in nude mice. Table shows that three BPLER lines derived from BPEC cells isolated from three different individuals each generated tumors having several orders of magnitude greater efficiency than HMLER cells derived from the same tissue donor. In some instances e.g., BPLER 2 cells, tumors were able to form with as little as 5 unsorted cells. B) Chart of tumor sphere forming efficiency of BPLER and HMLER tested by plating single cell suspensions (20,000 cells/well) of each cell line into 6-well ultra-low attachment plates (Corning). Multi-cellular tumor spheres were counted under the microscope at day 7. C) Western blot of three independent BPLER and HMLER lines probed with TSC markers CD166 and CD326, using B-actin as a loading control. D) Chart showing that FACS enriched CD44-high, CD166-high or CD326-high subpopulation of BPLER-2 cells were shown to form more tumor spheres than that of CD44-low, CD166-low, or CD326-low cell subpopulations. E) Chart showing that in each independently derived BPLER cell line (e.g., BPLER2, BPLER3 and BPLER4) the TSC enriched FACS sorted CD44-high/CD166-high cell subpopulations formed more tumor spheres than that of the CD44-low/CD166-low non-stem tumor cell (non-STC) subpopulations. F) Chart showing that in multiple cancer cell lines, including triple-negative breast cancer cell lines SUM-159 and MDB-MB-23 and ovarian cancer cell lines SKOV3 and OV-90, the TSC enriched FACS sorted CD44-high/CD166-high cell subpopulations formed more tumor spheres than the CD44-low/CD166-low non-STC subpopulations.

As described herein, a variety of methods and compositions are envisioned relating to the discovery that tumor stem cells demonstrate an increased level or activity of HDAC1, HDAC7 (particularly a phosphorylated form of HDAC7), or both HDAC1 and HDAC7 as compared with non-stem tumor cells. In describing these methods and compositions, certain terms and phrases are used throughout as follows.

I. Definitions

The term "antibody" encompasses immunoglobulins and derivatives thereof containing an immunoglobulin domain capable of binding to an antigen. An antibody can originate from a mammalian or avian species, e.g., human, rodent (e.g., mouse, rabbit), goat, chicken, etc., or can be generated ex vivo using a technique such as phage display. Antibodies include members of the various immunoglobulin classes, e.g., IgG, IgM, IgA, IgD, IgE, or subclasses thereof such as IgG1, IgG2, etc. In various embodiments of the invention "antibody" refers to an antibody fragment or molecule such as an Fab', F(ab')2, scFv (single-chain variable) that retains an antigen binding site and encompasses recombinant molecules comprising one or more variable domains (VH or VL). An antibody can be monovalent, bivalent or multivalent in various embodiments. The antibody may be a chimeric or "humanized" antibody. An antibody may be polyclonal or monoclonal, though monoclonal antibodies may be preferred. In some aspects, an antibody is an intrabody, which may be expressed intracellularly.

An "effective amount" or "effective dose" of a compound or other agent (or composition containing such compound or agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular compound, agent, or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or the desired effect may be achieved by use of multiple doses. An effective amount of a composition may be an amount sufficient to reduce the severity of or prevent one or more symptoms or signs of a disorder.

"Contacting", "contacting the cell" and any derivations thereof as used herein, refers to any means of introducing an agent (e.g., nucleic acids, oligopeptides, ribozymes, antibodies, small molecules, etc) into a target cell, including chemical and physical means, whether directly or indirectly or whether the agent physically contacts the cell directly or is introduced into an environment in which the cell is present. Contacting also is intended to encompass methods of exposing a cell, delivering to a cell, or 'loading' a cell with an agent by viral or non-viral vectors, and wherein such agent is bioactive upon delivery. The method of delivery will be chosen for the particular agent and use (e.g., cancer being treated). Parameters that affect delivery, as is known in the medical art, can include, inter alia, the cell type affected (e.g. tumor), and cellular location. In some embodiments, contacting includes administering the agent to a subject. In some embodiments, contacting refers to exposing a cell or an environment in which the cell is located to one or more HDAC inhibitors of the present invention.

"Identity" or "percent identity" is a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., generate alignments. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.)

"Isolated" refers to a substance that is separated from at least some other substances with which it is normally found in nature, usually by a process involving the hand of man, or is artificially produced, e.g., chemically synthesized, or present in an artificial environment. In some embodiments, any of the nucleic acids, polypeptides, nucleic-acid-protein structures, protein complexes, or cells of the invention, is isolated. In some embodiments, an isolated nucleic acid is a nucleic acid that has been synthesized using recombinant nucleic acid techniques or in vitro transcription or chemical synthesis or PCR. In some embodiments, an isolated polypeptide is a polypeptide that has been synthesized using recombinant nucleic acid techniques or in vitro translation or chemical synthesis.

"Nucleic acid" is used interchangeably with "polynucleotide" and encompasses naturally occurring polymers of nucleosides, such as DNA and RNA, usually linked by phosphodiester bonds, and non-naturally occurring polymers of nucleosides or nucleoside analogs. In some embodiments a nucleic acid comprises standard nucleotides (abbreviated A, G, C, T, U). In other embodiments a nucleic acid comprises one or more non-standard nucleotides. In some embodiments, one or more nucleotides are non-naturally occurring nucleotides or nucleotide analogs. A nucleic acid can be single-stranded or double-stranded in various embodiments of the invention. A nucleic acid can comprise chemically or biologically modified bases (for example, methylated bases), modified sugars (2'-fluororibose, arabinose, or hexose), modified phosphate groups (for example, phosphorothioates or 5'-N-phosphoramidite linkages), locked nucleic acids, or morpholinos. In some embodiments, a nucleic acid comprises nucleosides that are linked by phosphodiester bonds. In some embodiments, at least some nucleosides are linked by a non-phosphodiester bond. A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications), non-standard nucleotides, delivery vehicles and approaches, etc., known in the art as being useful in the context of RNA interference (RNAi), aptamer, or antisense-based molecules for research or therapeutic purposes are contemplated for use in various embodiments of the instant invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. A nucleic acid may comprise a detectable label, e.g., a fluorescent dye, radioactive atom, etc. "Oligonucleotide" refers to a relatively short nucleic acid, e.g., typically between about 4 and about 60 nucleotides long. The terms "polynucleotide sequence" or "nucleic acid sequence" as used herein can refer to the nucleic acid material itself and is not restricted to the sequence information (i.e. the succession of letters chosen among the five base letters A, G, C, T, or U) that biochemically characterizes a specific nucleic acid, e.g., a DNA or RNA molecule. A naturally occurring nucleic acid or a nucleic acid identical in sequence to a naturally occurring nucleic acid may be referred to herein as a "native nucleic acid", a "native XXX nucleic" (where XXX represents the name of the nucleic acid), or simply by the name of the nucleic acid or gene.

A "polypeptide" refers to a polymer of amino acids linked by peptide bonds. A protein is a molecule comprising one or more polypeptides. A peptide is a relatively short polypeptide, typically between about 2 and 60 amino acids in length. The terms "protein", "polypeptide", and "peptide" may be used interchangeably.

A "multisubunit protein" is composed of multiple polypeptide chains physically associated with one another to form a complex. Polypeptides of interest herein often contain standard amino acids (the 20 L-amino acids that are most commonly found in nature in proteins). However, other amino acids and/or amino acid analogs known in the art can be used in certain embodiments of the invention. One or more of the amino acids in a polypeptide (e.g., at the N- or C-terminus or in a side chain) may be altered, for example, by addition, e.g., covalent linkage, of a moiety such as an alkyl group, carbohydrate group, a phosphate group, a halogen, a linker for conjugation, etc. A polypeptide sequence presented herein is presented in an N-terminal to C-terminal direction unless otherwise indicated. "Polypeptide domain" refers to a segment of amino acids within a longer polypeptide. A polypeptide domain may exhibit one or more discrete binding or functional properties, e.g., a binding activity or a catalytic activity. A domain may be recognizable by its conservation among polypeptides found in multiple different species. The term "polypeptide sequence" or "amino acid sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. A naturally occurring polypeptide or a polypeptide identical in sequence to a naturally occurring polypeptide may be referred to herein as a "native polypeptide", a "native XXX polypeptide" (where XXX represents the name of the polypeptide), or simply by the name of the polypeptide.

A "variant" of a nucleic acid refers to a nucleic acid that differs by one or more nucleotide substitutions, additions, or deletions, relative to a native nucleic acid. An addition can be an insertion within the nucleic acid or an addition at the 5'- or 3'-terminus. A deletion can be a deletion of a 5'-terminal region, 3'-terminal region and/or an internal region. A "variant" of a polypeptide refers to a polypeptide that differs by one or more nucleotide amino acid substitutions, additions, or deletions, relative to a native polypeptide. An addition can be an insertion within the polypeptide or an addition at the N- or C-terminus. A deletion can be a deletion of an N-terminal region, a C-terminal region, and/or an internal region. In some embodiments, the number of nucleotides or amino acids substituted in and/or added to a native nucleic acid or polypeptide or portion thereof can be for example, about 1 to 30, e.g., about 1 to 20, e.g., about 1 to 10, e.g., about 1 to 5, e.g., 1, 2, 3, 4, or 5. In some embodiments, the number of nucleotides or amino acids substituted in and/or added to a native nucleic acid or polypeptide or portion thereof can be for example, between 0.1% and 10% of the total number of nucleotides or amino acids in such native nucleic acid or polypeptide or portion thereof. In some embodiments, a variant comprises a nucleic acid or polypeptide whose sequence is at least 20%, 30%, 40%, 50%, 60%, 70%, 80%, 85%, 90%, 95%, 96%, 97%, 98%, 99%, 99.5%, or more identical in sequence to a native nucleic acid polypeptide (e.g., from a vertebrate such as a human, mouse, rat, cow, or chicken) over at least 50, 100, 150, 200, 250, 300, 400, 450, or 500 amino acids (but is not identical in sequence to native nucleic acid or polypeptide). In some embodiments, a variant comprises a nucleic acid or polypeptide at least 20%, 30%, 40%, 50%, 60%, 70%, 80%, 85%, 90%, 95%, 96%, 97%, 98%, 99%, 99.5%, or more identical in sequence to a native nucleic acid or polypeptide (e.g., from a vertebrate such as a human, mouse, rat, cow, or chicken) over at least 20%, 30%, 40%, 50%, 60%, 70%, 80%, 85%, 90%, 95%, 96%, 97%, 98%, 99%, 99.5%, or 100% of the native nucleic acid or polypeptide. In some embodiments, a variant nucleic acid or polypeptide comprises or consists of a fragment. A fragment is a nucleic acid or polypeptide that is shorter than a particular nucleic acid polypeptide and is identical in sequence to the nucleic acid polypeptide over the length of the shorter nucleic acid or polypeptide. In some embodiments, a fragment is at least 50%, 60%, 70%, 80%, 85%, 90%, 95%, 96%, 97%, 98%, or 99% as long as a native nucleic acid or polypeptide.

In some embodiments, a polypeptide fragment is an N-terminal fragment (i.e., it lacks a C-terminal portion of the native polypeptide). In some embodiments, a fragment is a C-terminal fragment (i.e., it lacks an N-terminal portion of the native polypeptide). In some embodiments, a fragment is an internal fragment, i.e., it lacks an N-terminal portion and a C-terminal portion of the native polypeptide. In some embodiments, a variant comprises two fragments fused together, e.g., an N-terminal portion and a C-terminal portion.

In some embodiments, a variant polypeptide comprises a heterologous polypeptide portion. The heterologous portion often has a sequence that is not present in the native polypeptide. In some embodiments, a heterologous portion has a sequence that is present in the native polypeptide, but at a different position. For example, a domain can be duplicated or positioned at a different location within the polypeptide. A heterologous polypeptide portion may be, e.g., between 5 and about 5,000 amino acids long, or longer, respectively, in various embodiments. Often it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6×His, Flag, GST), solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a variant has a tag located at the N- or C-terminus, e.g., as an N- or C-terminal fusion. The polypeptide could comprise multiple tags. In some embodiments, a 6×His tag and a NUS tag are present, e.g., at the N-terminus. In some embodiments, a tag is cleavable, so that it can be removed from the polypeptide, e.g., by a protease. Exemplary proteases include, e.g., thrombin, TEV protease, Factor Xa, PreScission protease, etc. In some embodiments, a "self-cleaving" tag is used. See, e.g., PCT/US05/05763. Sequences encoding a tag can be located 5' or 3' with respect to a polynucleotide encoding the polypeptide (or both). In some embodiments, a heterologous portion comprises a detectable marker such as a fluorescent or luminescent protein, e.g., green, blue, sapphire, yellow, red, orange, and cyan fluorescent protein or derivatives thereof (e.g., EGFP, ECFP, EYFP), or monomeric red fluorescent protein or derivatives such as those known as "mFruits", e.g., mCherry, mStrawberry, mTomato, or Cerulean or DsRed. In some embodiments, a heterologous portion comprises an enzyme that catalyzes a reaction leading to a detectable reaction product in the presence of a suitable substrate. Examples include alkaline phosphatase, beta galactosidase, horseradish peroxidase, luciferase, to name a few. Often, a detectable marker or reaction product is optically detectable, emitting or absorbing electromagnetic radiation (e.g., within the visible or near infrared region of the spectrum) that can be observed visually and/or using suitable detection equipment. Detectable markers can include moieties that quench signals emitted from other moieties. In some embodiments, a heterologous portion comprises a selectable marker, e.g., a drug resistance marker or nutritional marker. Exemplary drug resistance markers include enzymes that inactivate compounds that would otherwise be cytotoxic or inhibit cell proliferation (e.g., neomycin or G418 resistance gene, puromycin resistance gene, blastocidin resistance gene etc.). A nutritional marker is typically an enzyme that permits a cell to survive in medium that lacks a particular nutrient. In some embodiments a tag or other heterologous portion is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, a domain that targets the polypeptide to a particular organelle, etc.

In some embodiments, a variant is a functional variant, i.e., the variant at least in part retains at least one biological activity of a native polypeptide, such as ability to bind to a particular molecule or structure, or ability to catalyze a biochemical reaction (or is a nucleic acid that encodes a functional variant polypeptide). One of skill in the art can readily generate functional variants or fragments. In some embodiments, a variant comprises one or more conservative amino acid substitutions relative to a native polypeptide. Conservative substitutions may be made on the basis of similarity in side chain size, polarity, charge, solubility, hydrophobicity, hydrophilicity and/or the amphipathic nature of the residues involved. As known in the art, such substitutions are, in general, more likely to result in a variant that retains activity as compared with non-conservative substitutions. In one embodiment, amino acids are classified as follows:

Special: C
Neutral and small: A, G, P, S, T
Polar and relatively small: N, D, Q, E
Polar and relatively large: R, H, K
Nonpolar and relatively small: I, L, M, V
Nonpolar and relatively large: F, W, Y
Special: C See, e.g., Zhang, J. J. Mol. Evol. 50:56-68, 2000). In some embodiments, proline (P) is considered to be in its own group as a second special amino acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution, deletion, or addition does not alter or delete or disrupt an amino acid or region of a polypeptide known or thought to be involved in or required for a particular activity that is desired to be maintained, while in other embodiments a substitution, deletion, or addition is selected to remove or disrupt a region known or thought be to in involved in or required for a particular activity. In some embodiments, an alteration is at an amino acid that differs among homologous polypeptides of different species. Variants could be tested in cell-free and/or cell-based assays to assess their activity.

In some embodiments, a variant or fragment that has substantially reduced activity as compared with the activity of native polypeptide (e.g., less than 10% of the activity of native polypeptide) is useful. For example, such polypeptide could interfere with the function of native polypeptide, e.g., by competing with native polypeptide, or serve as an immunogen for purposes of raising antibodies.

In some embodiments, a variant nucleic acid comprises a heterologous nucleic acid portion, which may be located at the 5'-terminus, 3'-terminus, or internally. The heterologous portion often has a sequence that is not present in the native nucleic acid. In some embodiments, a heterologous portion has a sequence that is present in the native nucleic acid, but at a different position. A heterologous nucleic acid portion may encode a heterologous polypeptide portion, such as any of those described above, or may not encode a polypeptide. A heterologous nucleic acid portion may or may not have a property or activity such as serving as an expression control element, recognition sequence for a DNA binding protein, or encoding a functional RNA.

As used herein, the term "purified" refers to agents or entities (e.g., compounds such as polypeptides, nucleic acids, small molecules, etc.) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 855%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and, optionally, at least some of the cellular material (e.g., cell wall, cell membrane(s), cell organelle(s)) has been removed. In some embodiments, any of the nucleic acids, polypeptides, nucleic-acid-protein structures, or protein complexes of the invention, is at least partly purified.

A "small molecule" as used herein, is an organic molecule that is less than about 2 kilodaltons (KDa) in mass. In some embodiments, the small molecule is less than about 1.5 KDa, or less than about 1 KDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

A "subject" can be any multicellular animal, e.g., a vertebrate, e.g., a mammal or avian. Exemplary mammals include, e.g., humans, non-human primates, rodents (e.g., mouse, rat, rabbit), ungulates (e.g., ovine, bovine, equine, caprine species), canines, and felines. In some embodiments, the animal is a mammal of economic importance, such as a cow, horse, pig, goat, or sheep.

In practicing the many aspects of the invention herein, samples e.g., biological samples can be selected from many sources such as tissue biopsy (including cell sample or cells cultured therefrom; biopsy of bone marrow or solid tissue, for example cells from a solid tumor), blood, blood cells (red blood cells or white blood cells), serum, plasma, lymph, ascetic fluid, cystic fluid, urine, sputum, stool, saliva, bronchial aspirate, CSF or hair. Cells from a sample can be used, or a lysate of a cell sample can be used. In certain embodiments, the biological sample is a tissue biopsy cell sample or cells cultured therefrom, for example, cells removed from a solid tumor or a lysate of the cell sample. In certain embodiments, the biological sample comprises blood cells.

"Treat", "treating" and similar terms refer to providing medical and/or surgical management of a subject. Treatment can include, but is not limited to, administering a compound or composition (e.g., a pharmaceutical composition or a composition comprising appropriate cells in the case of cell-based therapy) to a subject. Treatment is typically undertaken in an effort to alter the course of a disorder (which term is used to refer to a disease, syndrome, or abnormal condition) or undesirable or harmful condition in a manner beneficial to the subject. The effect of treatment can generally include reversing, alleviating, reducing severity of, delaying the onset of, curing, inhibiting the progression of, and/or reducing the likelihood of occurrence or reoccurrence of the disorder or condition, or one or more symptoms or manifestations of such disorder or condition. A composition can be administered to a subject who has developed a disorder or is at risk of developing a disorder. A composition can be administered prophylactically, i.e., before development of any symptom or manifestation of a disorder. Typically in this case the subject will be at increased risk of developing the disorder relative to a member of the general population. For example, a composition can be administered to a subject with a risk factor, e.g., a mutation in a gene, wherein the risk factor is associated with increased likelihood of developing the disorder but before the subject has developed symptoms or manifestations of the disorder. "Preventing" can refer to administering a composition to a subject who has not developed a disorder, so as to reduce the likelihood that the disorder will occur or so as to reduce the severity of the disorder should it occur. The subject may be identified (e.g., diagnosed by a medical practitioner) as having or being at risk of developing the disorder (e.g., at increased risk relative to many most other members of the population or as having a risk factor that increases likelihood of developing the disorder).

Pharmaceutical compositions for use in the present invention can include compositions comprising one or a combination of HDAC inhibitors in an effective amount to achieve the intended purpose. The determination of an effective dose of a pharmaceutical composition of the invention is well within the capability of those skilled in the art. A therapeutically effective dose refers to that amount of active ingredient which ameliorates the symptoms or condition. Therapeutic efficacy and toxicity can be determined by standard pharmaceutical procedures in cell cultures or experimental animals, for example the ED50 (the dose therapeutically effective in 50% of the population) and LD50 (the dose lethal to 50% of the population).

As used herein "HDAC" or "HDAC protein" refers generally to a family of proteins involved in the deacetylation of histones. More specifically, "HDAC" includes histone deaceytlase-1 (HDAC1), histone deacetylase-7 (HDAC7), and phosphorylated HDAC7.

As used herein "HDAC1 overexpression", "HDAC7 overexpression", "phosphorylated HDAC7 overexpression" and "increased level and/or activity of HDAC1, HDAC7, and/or phosphorylated HDAC7" is meant to encompass a level and/or activity of HDAC1, HDAC7, and/or phosphorylated HDAC7 protein that is at least about 1, 2, 3, 4, 5, 6, 7, 8, 9, 10 fold or more higher than a reference or normal level and/or activity of HDAC1, HDAC7, and/or phosphorylated HDAC7 protein. However, modest increased levels and/or activity, such as about 0.1, 0.2, 0.3, 0.4, 0.5, 0.6, 0.7, 0.8, 0.9 fold higher levels and/or activity than a reference or normal level or activity of HDAC1, HDAC7 and/or phosphorylated HDAC7 are also encompassed by this phrase.

As used herein "HDAC inhibitor" and "HDAC inhibitors" refer to inhibitors of HDAC1, HDAC7, and/or phosphorylated HDAC7, including agents that inhibit the level and/or activity of HDAC1 and/or HDAC7 and/or phosphorylated HDAC7, as well as agents that inhibit the phosphorylation of HDAC7 e.g., inhibitors of EMK protein kinase, C-TAK1 protein kinase, and/or CAMK protein kinase, and agents that activate or increase the level and/or activity of phosphatase activity to remove phosphoryl groups from HDAC7 e.g., activators of PP2A phosphatase and/or myosin phosphatase. In some embodiments, HDAC inhibitors include molecules that bind directly to a functional region of HDAC1 and/or HDAC7 and/or phosphorylated HDAC7 in a manner that interferes with the enzymatic activity of HDAC1 and/or HDAC7 and/or phosphorylated HDAC7 e.g., agents that interfere with substrate binding to HDAC1 and/or HDAC7 and/or phosphorylated HDAC7. In some embodiments, HDAC inhibitors include molecules that bind directly to HDAC7 in a manner that prevents the phosphorylation of HDAC7. HDAC inhibitors include agents that inhibit the activity of peptides, polypeptides, or proteins that modulate the activity of HDAC1 and/or HDAC7 e.g., inhibitors of EMK protein kinase, C-TAK1 kinase, CAMK protein kinase inhibitors of C-TAK1 protein kinase. Examples of suitable inhibitors include, but are not limited to antisense oligonucleotides, oligopeptides, interfering RNA e.g., small interfering RNA (siRNA), small hairpin RNA (shRNA), aptamers, ribozymes, small molecule inhibitors, or antibodies or fragments thereof, and combinations thereof. In some embodiments, HDAC inhibitors are specific inhibitors or specifically inhibit the level and/or activity of HDAC1 and/or HDAC7 and/or phosphorylated HDAC7. As used herein, "specific inhibitor(s)" refers to inhibitors characterized by their ability to bind to with high affinity and high specificity to HDAC1 and/or HDAC7 and/or phoshphorylated HDAC7 proteins or domains, motifs, or fragments thereof, or variants thereof, and preferably have little or no binding affinity for non-HDAC1 and/or non-HDAC7 and/or non-phosphorylated HDAC7 proteins. As used herein, "specifically inhibit(s)" refers to the ability of an HDAC inhibitor of the present invention to inhibit the level and/or activity of a target polypeptide e.g., HDAC1, and/or HDAC7, and/or phosphorylated HDAC7, and/or EMK protein kinase, and/or C-TAK1 protein kinase and/or CAMK protein kinase and preferably have little or no inhibitory effect on non-target polypeptides. As used herein, "specifically activate(s)" and "specifically increase(s)" refers to the ability of an HDAC inhibitor of the present invention to stimulate (e.g., activate or increase) the level and/or activity of a target polypeptide, e.g., PP2A phosphatase and/or myosin phosphatase and preferably to have little or no stimulatory effect on non-target polypeptides.

As used herein "level", refers to a measure of the amount of, or a concentration of a transcription product, for instance an mRNA, or a translation product, for instance a protein or polypeptide.

As used herein "activity" refers to a measure for the ability of a transcription product or a translation product to produce a biological effect or a measure for a level of biologically active molecules.

As used herein"level and/or activity" further refer to gene expression levels or gene activity. Gene expression can be defined as the utilization of the information contained in a gene by transcription and translation leading to the production of a gene product.

As used herein, the term "downregulating HDAC expression" refers to a substantial reduction e.g., measurable or observable, in the expression of the HDAC protein in a target cell through any of the methods disclosed herein or those known to one of ordinary skill in the art, with the benefit of the present disclosure.

As used herein, the term "inhibiting HDAC translation" refers to a substantial reduction e.g., measurable or observable, in the translation of the HDAC protein in the target cell from RNA encoding the HDAC protein, including RNA natively transcribed by the target cell and RNA artificially introduced into the target cell.

As used herein, the term "inhibiting HDAC enzymatic activity" refers to a substantial reduction e.g., measurable or observable, in the ability of HDAC to act as an enzyme (i.e. have a designated effect on one or more substrate molecules) through any of the methods disclosed herein or those known to one of ordinary skill in the art, with the benefit of the present disclosure.

In some embodiments, the present disclosure provides a method for treating cancer comprising inhibiting HDAC. In some embodiments, the inhibition of HDAC may comprise downregulating HDAC expression. Suitable methods for downregulating HDAC expression may include: inhibiting transcription of HDAC mRNA; degrading HDAC mRNA by methods including, but not limited to, the use of interfering RNA (RNAi); blocking translation of HDAC mRNA by methods including, but not limited to, the use of antisense nucleic acids or ribozymes, or the like. In some embodiments, a suitable method for downregulating HDAC expression may include providing to the cancer a small interfering RNA (siRNA) targeted to HDAC. In some embodiments, such a small molecule may comprise staurosporine. In some embodiments, suitable methods for down-regulating HDAC may include administering a small molecule inhibitor of HDAC. In some embodiments, such a small molecule may comprise Trichostatin A. In some embodiments, it may be advantageous to use two or more of these methods simultaneously or in series. One of ordinary skill in the art, with the benefit of the present disclosure, may recognize suitable methods for downregulating HDAC expression that are still considered within the scope of the present disclosure.

As used herein, "solid tumor" is intended to encompass those solid tumors from which solid tumor stem cells can be isolated or enriched including, but not limited to, the following sarcomas and carcinomas: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Solid tumor is also intended to encompass epithelial cancers.

As used herein, "tumor stem cell" includes fibrosarcoma tumor stem cells, myxosarcoma tumor stem cells, liposarcoma tumor stem cells, chondrosarcoma tumor stem cells, osteogenic sarcoma tumor stem cells, chordoma tumor stem cells, angiosarcoma tumor stem cells, endotheliosarcoma tumor stem cells, lymphangiosarcoma tumor stem cells, lymphangioendotheliosarcoma tumor stem cells, synovioma tumor stem cells, mesothelioma tumor stem cells, Ewing's tumor stem cells, leiomyosarcoma tumor stem cells, rhabdomyosarcoma tumor stem cells, colon carcinoma tumor stem cells, pancreatic cancer tumor stem cells, breast cancer tumor stem cells, ovarian cancer tumor stem cells, prostate cancer tumor stem cells, squamous cell carcinoma tumor stem cells, basal cell carcinoma tumor stem cells, adenocarcinoma tumor stem cells, sweat gland carcinoma tumor stem cells, sebaceous gland carcinoma tumor stem cells, papillary carcinoma tumor stem cells, papillary adenocarcinomas tumor stem cells, cystadenocarcinoma tumor stem cells, medullary carcinoma tumor stem cells, bronchogenic carcinoma tumor stem cells, renal cell carcinoma tumor stem cells, hepatoma tumor stem cells, bile duct carcinoma tumor stem cells, choriocarcinoma tumor stem cells, seminoma tumor stem cells, embryonal carcinoma tumor stem cells, Wilms' tumor stem cells, cervical cancer tumor stem cells, testicular tumor stem cells, lung carcinoma tumor stem cells, small cell lung carcinoma tumor stem cells, bladder carcinoma tumor stem cells, epithelial carcinoma tumor stem cells, glioma tumor stem cells, astrocytoma tumor stem cells, medulloblastoma tumor stem cells, craniopharyngioma tumor stem cells, ependymoma tumor stem cells, pinealoma tumor stem cells, hemangioblastoma tumor stem cells, acoustic neuroma tumor stem cells, oligodendroglioma tumor stem cells, meningioma tumor stem cells, melanoma tumor stem cells, neuroblastoma tumor stem cells, and retinoblastoma tumor stem cells. Tumor stem cell also is intended to encompass epithelial cancer tumor stem cells, haematopoietic tumor stem cells, including hematological tumor stem cells, e.g., tumor stem cells associated with leukemias, myelomas, and/or lymphomas; etc.

II. Methods for Targeting Tumor Stem Cells

Tumor stem cells are a subpopulation of human tumor cells that exhibit the capacity for tumor initiation, self-renewal and differentiation. Understanding how tumor stem cells respond to anti-cancer agents may help elucidate the cellular mechanisms essential for developing novel therapeutic approaches to targeting tumors e.g., tumor stem cells. The invention relates in part to the discovery that tumor stem cells exhibit increased levels of HDAC1, HDAC7 and phosphorylated HDAC7 protein. As described in further detail in the Examples, using a solid tumor model (e.g., breast, ovarian, colon) of isogenic stem and non-stem like cells it was observed that tumor stem cells are significantly more sensitive to histone deacetylase (HDAC) inhibitors than non stem tumor cells. Such sensitivity significantly correlated with increased expression of HDAC1 and/or HDAC7 and/or phosphorylated HDAC7 in the tumor stem cell subpopulation. Consistent with these results, knockdown of HDAC1 and/or HDAC7 was observed to decrease tumor cell proliferation, tumor sphere formation and soft agar colony formation. Accordingly, HDAC1 and/or HDAC7 and/or phosphorylated HDAC7 are suitable targets for solid tumor treatment, including inhibiting the proliferation of tumor stem cells, as well as inhibiting the formation of tumor spheres.

In some aspects, the invention provides for methods of inhibiting the proliferation of and/or the elimination of one or more tumor stem cell, the method including contacting the cell with an effective amount of an HDAC inhibitor. Inhibiting the proliferation of, and/or eliminating one or more tumor stem cells can be useful for the treatment of solid tumors. In some embodiments, inhibiting proliferation of one or more tumor stem cells can lead to one or more results including, but not limited to, transforming the one or more tumor stem cells into non-stem tumor cells, reducing the growth rate of a tumor containing the tumor stem cells, reducing the overall growth of the tumor containing the tumor stem cells, reducing the amount of tumor stem cells present in the tumor containing the tumor stem cells, reducing the accumulation of tumor stem cells in the tumor containing the tumor stem cells, reducing the capacity for the tumor stem cells to generate new tumor stem cells, or reducing the capacity for the tumor stem cells to divide or form new tumor cells. In some embodiments, transforming one or more tumor stem cells into non-stem tumor cells gives the tumor stem cell a finite life and strips the tumor stem cell of its capacity for tumor initiation, self-renewal, and differentiation. Accordingly, transforming one or more tumor stem cells into non-stem tumor cells may allow a patient receiving an HDAC inhibitor of the present invention to outlive the non-stem tumor cells e.g., transformed tumor stem cells. In some embodiments, the method of inhibiting the proliferation of tumor stem cells eliminates e.g., kills, tumor stem cells in the tumor containing the tumor stem cells. In one embodiment, the method of inhibiting the proliferation of tumor stem cells is useful for increasing a patient's progression free survival time.

In some embodiments, the inhibiting the proliferation of the one or more tumor stem cells includes inhibiting and/or eliminating a significant fraction of the tumor stem cells present in a tumor containing the tumor stem cells. In some embodiments, a significant fraction includes a majority of the tumor stem cell population present in the tumor. In some embodiments, a significant fraction comprises at least 1%, 10%, 20%, 30%, 40%, 50%, 60%, 70%, 80%, 85%, 90%, 95%, 96%, 97%, 98%, 99%, 99.5%, or up to about 100% of the tumor stem cells contained within a tumor. In one embodiment, a significant fraction includes up to about 100% of the tumor stem cell population present in the tumor. In one embodiment, a significant fraction includes 100% of the tumor stem cell population present in the tumor.

In some embodiments, the HDAC inhibitor specifically inhibits the level and/or activity of HDAC1 protein. In some embodiments, the HDAC inhibitor specifically inhibits the level and/or activity of HDAC7 protein. In some embodiments, the HDAC inhibitor specifically inhibits the level and/or activity of phosphorylated HDAC7 protein.

In some aspects, a method of inhibiting the proliferation of one or more tumor stem cell comprises contacting the cell with both at least one HDAC1 inhibitor and at least one HDAC7 inhibitor. In some embodiments, the contacting occurs simultaneously. In some embodiments, the contacting is occurs near simultaneously. In some embodiments, the HDAC1 and HDAC7 inhibitors specifically inhibit the level and/or activity of both HDAC1 and HDAC7 protein. In some embodiments, the HDAC1 and HDAC7 inhibitor specifically inhibits the level and/or activity of both HDAC1 and phosphorylated HDAC7 protein.

In some aspects, the HDAC inhibitor inhibits the level and/or activity of a protein kinase believed to be responsible for the phosphorylation, e.g., activation, of HDAC7. Strategies for inhibiting the level and/or activity of protein kinases can be performed by those of ordinary skill in the art without undue experimentation. Suitable strategies for inhibiting protein kinases include inhibiting the enzymatic activity of the protein kinase itself e.g., phosphorylation, blocking the phosphorylation site of the protein kinase e.g., using a binding molecule e.g., oligopeptide as described below, that binds with specificity and affinity to the site at which HDAC7 is phosphorylated (e.g., serine-155), reducing the level of expression of the protein kinase itself, and combinations thereof. In some embodiments, the HDAC inhibitor specifically inhibits the level and/or activity of EMK protein kinase. In some embodiments, the HDAC inhibitor specifically inhibits the level and/or activity of C-TAK1 protein kinase. In some embodiments, the HDAC inhibitor specifically inhibits the level and/or activity of CaMK protein kinase.

In other aspects, the HDAC inhibitor stimulates the level and/or activity of a protein phosphatase believed to be responsible for the dephosphorylation, e.g., of HDAC7. Strategies for stimulating the level and/or activity of protein phosphatases can be performed by those of skill in the art without undue experimentation. In some embodiments, the HDAC inhibitor specifically increases the level and/or activity of PP2A phosphatase. In some embodiments, the HDAC inhibitor specifically increases the level and/or activity of myosin phosphatase.

In some embodiments, the cell is a breast cell. In some embodiments, the cell is an ovarian cell. In some embodiments, the cell is a colon cell. In some embodiments, the cell is a brain cell. In some embodiments, the cell is a pancreatic cell. In some embodiments, the cell is a prostate cell. In some embodiments, the cell is a lung cell. In some embodiments, the cell is a solid tumor cell. In some embodiments, the cell is a hematological tumor cell. In some embodiments, the cell is obtained from a human subject.

Examples of suitable HDAC inhibitors that can be used for inhibiting the proliferation of tumor stem cells include, but are not limited to nucleic acids e.g., antisense nucleic acids, oligopeptides, aptamers, ribozymes, small molecules, and antibodies or fragments thereof, and combinations thereof.

One of skill in the art will also readily be able to obtain amino acid sequences of HDAC1 and/or HDAC7 polypeptides, and the genomic and mRNA sequences encoding them, from publicly available databases, such as those available at the National Center for Biotechnology Information (NCBI; www.ncbi.nlm.nih.gov), e.g., Gene, GenBank, Proteins, etc. For example, the Gene database provides sequence information (e.g., accession numbers for reference sequences) and functional information, which can be obtained, e.g., by searching on a name or Gene ID for a gene or protein of interest. In addition, HDAC1 and HDAC7 protein sequences, and nucleic acid constructs encoding them, are described in the scientific literature and available from a variety of sources. One of skill in the art can readily generate HDAC inhibitors of the present invention using the sequence and functional information obtained via these publicly available databases using the techniques and methods disclosed herein.

Table 1 provides a list of the official symbol and Gene ID of HDAC1, HDAC7, EMK, and C-TAK1, CaMK, PP2A and myosin phosphatase polypeptides of interest.

TABLE 1

Human genes encoding selected HDAC associated polypeptides

| Name | Official Symbol/ Alternate symbol | Gene ID |
|---|---|---|
| histone deacetylase 1 | HDAC1 | 3065 |
| histone deacetylase 7 | HDAC7 (also called HDAC7A) | 51564 |
| MAP/microtubule affinity-regulating kinase 2 | EMK1 (also called PAR1 and MARK2) | 2011 |
| MAP/microtubule affinity-regulating kinase 3 | C-TAK1 (also called PAR1A and MARK3) | 4140 |
| Calcium/calmodulin-dependent protein kinase II gamma | CAMK2G (also called CAMK | 818 |
| Protein phosphatase 2A activator, regulatory subunit 4 | PPP2R4 (also called PP2A) | 5524 |
| Protein phosphatase 1, regulatory (inhibitor) subunit 12A | PPP1R12A (also called myosin phosphatase | 4659 |

In some aspects, nucleic acids that can inhibit the expression and/or translation of HDAC1 and/or HDAC7 can also be used as inhibitors of HDAC1 and/or HDAC7 and/or phosphorylated HDAC7. Such inhibitory nucleic acids can hybridize to a HDAC1 and/or HDAC7 nucleic acid under intracellular or stringent conditions. The inhibitory nucleic acid is capable of reducing expression or translation of a nucleic acid encoding the HDAC1 and/or HDAC7. A nucleic acid encoding a HDAC1 and/or HDAC7 may be genomic DNA as well as messenger RNA. It may be incorporated into a plasmid vector or viral DNA. It may be single strand or double strand, circular or linear.

An inhibitory nucleic acid is a polymer of ribose nucleotides or deoxyribose nucleotides having more than three nucleotides in length. An inhibitory nucleic acid may include naturally-occurring nucleotides; synthetic, modified, or pseudo-nucleotides such as phosphorothiolates; as well as nucleotides having a detectable label such as $P^{32}$, biotin, fluorescent dye or digoxigenin. An inhibitory nucleic acid that can reduce the expression and/or activity of an HDAC1 and/or HDAC7 nucleic acid may be completely complementary to the HDAC1 and/or HDAC7 nucleic acid. Alternatively, some variability between the sequences may be permitted. In some embodiments, an inhibitory nucleic acid that can reduce the expression and/or activity of an HDAC1 and/or HDAC7 nucleic acid may be complementary to HDAC1 and/or HDAC7 nucleic acid variants. In some embodiments, the inhibitor nucleic acid may be complementary to EMK and/or CTAK-1 and/or CaMK nucleic acid or variants thereof to reduce the activity of phosphorylated HDAC7 by reducing the expression and/or activity of EMK and/or CTAK-1 and/or CaMK.

An inhibitory nucleic acid of the invention can hybridize to a HDAC1 and/or HDAC7 nucleic acid under intracellular conditions or under stringent hybridization conditions. The inhibitory nucleic acids of the invention are sufficiently complementary to endogenous HDAC1 and/or HDAC7 nucleic acids to inhibit expression of a HDAC1 and/or HDAC7 nucleic acid under either or both conditions. Intracellular conditions refer to conditions such as temperature, pH and salt concentrations typically found inside a cell, e.g. a mammalian cell. One example of such a mammalian cell is a cancer cell (e.g., a tumor stem cell), or any cell where HDAC1 and/or HDAC7 is or may be expressed.

Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory nucleic acids that comprise, for example, 2, 3, 4, or 5 or more stretches of contiguous nucleotides that are precisely complementary to a HDAC1 and/or HDAC7 coding sequence, each separated by a stretch of contiguous nucleotides that are not complementary to adjacent coding sequences, may inhibit the function of a HDAC1 and/or HDAC7 nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to a sense nucleic acid to estimate the degree of mismatching that will be tolerated for inhibiting expression of a particular target nucleic acid. Inhibitory nucleic acids of the invention include, for example, a ribozyme or an antisense nucleic acid molecule.

The antisense nucleic acid molecule may be single or double stranded (e.g. a small interfering RNA (siRNA)), and may function in an enzyme-dependent manner or by steric blocking. Antisense molecules that function in an enzyme-dependent manner include forms dependent on RNase H activity to degrade target mRNA. These include single-stranded DNA, RNA and phosphorothioate molecules, as well as the double-stranded RNAi/siRNA system that involves target mRNA recognition through sense-antisense strand pairing followed by degradation of the target mRNA by the RNA-induced silencing complex. Steric blocking antisense, which are RNase-H independent, interferes with gene expression or other mRNA-dependent cellular processes by binding to a target mRNA and interfering with other processes. Steric blocking antisense includes 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce HDAC1 and/or HDAC7 translation such that the level of HDAC1 and/or HDAC7 and/or phosphorylated HDAC7 polypeptide is reduced. siRNAs mediate post-transcriptional gene silencing in a sequence-specific manner. See, for example, http://www.ambion.com/techlib/hottopics/rnai/rnai_may2002 print.html. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the HDAC1 and/or HDAC7 mRNA transcript. The region of homology may be 30 nucleotides or less in length, less than 25 nucleotides, about 21 to 23 nucleotides in length or less, e.g., 19 nucleotides in length. SiRNA is typically double stranded and may have nucleotide 3' overhangs. The 3' overhangs may be up to about 5 or 6 nucleotide '3 overhangs, e.g., two nucleotide 3' overhangs, such as, 3' overhanging UU dinucleotides, for example. In some embodiments, the siRNAs may not include any nucleotide 3' overhangs. Methods for designing siRNAs are known to those skilled in the art. See, for example, Elbashir et al. Nature 411: 494-498 (2001); Harborth et al. Antisense Nucleic Acid Drug Dev. 13: 83-106 (2003). Typically, a target site is selected that begins with AA, has 3' UU overhangs for both the sense and antisense siRNA strands, and has an approximate 50% G/C content. siRNAs may be chemically synthesized, created by in vitro transcription, or expressed from an siRNA expression vector or a PCR expression cassette. See, e.g., http://www.ambion.com/techlib/tb/tb.sub.—506html.

When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be any appropriate length, for example, up to 30 nucleotides in length, e.g., 3 to 23 nucleotides in length, and may be of various nucleotide sequences. SiRNAs also may be produced in vivo by cleavage of double-stranded RNA introduced directly or via a transgene or virus. Amplification by an RNA-dependent RNA polymerase may occur in some organisms. The siRNA may be further modified according to any methods known to those having ordinary skill in the art.

An antisense inhibitory nucleic acid may also be used to specifically reduce HDAC1 and/or HDAC7 expression, for example, by inhibiting transcription and/or translation. An antisense inhibitory nucleic acid is complementary to a sense nucleic acid encoding a HDAC1 and/or HDAC7. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding an HDAC1 and/or HDAC7. The non-coding region includes the 5' and 3' regions that flank the coding region, for example, the 5' and 3' untranslated sequences. An antisense inhibitory nucleic acid is generally at least six nucleotides in length, but may be up to about 8, 12, 15, 20, 25, 30, 35, 40, 45, or 50 nucleotides long. Longer inhibitory nucleic acids may also be used.

An antisense inhibitory nucleic acid may be prepared using methods known in the art, for example, by expression from an expression vector encoding the antisense inhibitory nucleic acid or from an expression cassette. Alternatively, it may be prepared by chemical synthesis using naturally-occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the antisense inhibitory nucleic acid and the sense nucleic acid.

Naturally-occurring nucleotides include the ribose or deoxyribose nucleotides adenosine, guanine, cytosine, thymine and uracil. Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5oxyacetic acid, butoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl)uracil, (acp3) w, and 2,6-diaminopurine.

Thus, inhibitory nucleic acids of the invention may include modified nucleotides, as well as natural nucleotides such as combinations of ribose and deoxyribose nucleotides, and an antisense inhibitory nucleic acid of the invention may be of any length discussed above and that is complementary to the nucleic acid sequences of HDAC1 and/or HDAC7 or variants thereof. In some embodiments, the antisense inhibitory nucleic acids of the invention may be of any length discussed above and that is complementary to the nucleic acid sequences of EMK and/or CTAK-1 and/or CaMK or variants thereof.

In some embodiments, an HDAC inhibitor of the present invention is a small hairpin RNA or short hairpin RNA (shRNA). Table 2 below lists commercially available (Sigma) shRNA vectors useful for interfering with HDAC1 and/or HDAC7 mRNA.

TABLE 2 shRNA Vectors for HDAC1 and HDAC7 mRNA

| | ID | Sequence |
|---|---|---|
| HDAC7 shRNA 1 | V2HS96399 | CTTCTCGTGAGCTAAAGAA (SEQ ID NO. 1) |
| HDAC7 shRNA 2 | V2HS96400 | CCAGCAAGATCCTCATTGT (SEQ ID NO. 2) |
| HDAC7 shRNA 3 | V2HS96401 | GCTACCATGTTTCTGCCAA (SEQ ID NO. 3) |
| HDAC7 shRNA 4 | V2HS262107 | CTACCATGTTTCTGCCAAA (SEQ ID NO. 4) |

TABLE 2-continued shRNA Vectors for HDAC1 and HDAC7 mRNA

| ID | Sequence |
|---|---|
| HDAC1 shRNA 1 TRCN195467 | CGGTTAGGTTGCTTCAATCTA (SEQ ID NO. 5) |
| HDAC1 shRNA 2 TRCN195103 | CCTAATGAGCTTCCATACAAT (SEQ ID NO. 6) |
| HDAC1 shRNA 3 TRCN195672 | CCACAGCGATGACTACATTAA (SEQ ID NO. 7) |
| HDAC1 shRNA 4 TRCN197198 | CCGGGCAACCATAAGACAAACTCCT (SEQ ID NO. 8) | shRNA is a sequence of RNA that makes a tight hairpin turn that can be used to silence gene expression by means of RNA interference. The shRNA hairpin structure is cleaved by the cellular machinery into a siRNA, which then binds to and cleaves the target mRNA. shRNA can be introduced into cells via a vector encoding the shRNA, where the shRNA coding region is operably linked to a promoter. The selected promoter permits expression of the shRNA. For example, the promoter can be a U6 promoter, which is useful for continuous expression of the shRNA. The vector can, for example, be passed on to daughter cells, allowing the gene silencing to be inherited. See, McIntyre G, Fanning G, Design and cloning strategies for constructing shRNA expression vectors, BMC BIOTECHNOL. 6:1 (2006); Paddison et al., Short hairpin RNAs (shRNAs) induce sequence-specific silencing in mammalian cells, GENES DEV. 16 (8): 948-58 (2002).

In some embodiments, an HDAC inhibitor of the present invention is a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave an HDAC1 and/or HDAC7 mRNA transcript and thereby inhibit translation of the mRNA. See, for example, Haseloff et al., U.S. Pat. No. 5,641,673. A ribozyme having specificity for a HDAC1 and/or HDAC7 nucleic acid or variant thereof may be designed based on the publicly available nucleotide sequences of HDAC1 and/or HDAC7. In some embodiments, ribozymes having specificity for EMK and/or CTAK-1 and/or CaMK nucleic acids or variants thereof can be designed based on the publicly available nucleotide sequences of EMK and/or CTAK-1 and/or CaMK.

Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from the nucleotide sequence of HDAC1 and/or HDAC7 and/or EMK and/or CTAK-1 and/or CaMK. Longer complementary sequences may be used to increase the affinity of the hybridization sequence for the target.

The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a HDAC1 and/or HDAC7 nucleic acid of the invention by modifying the hybridization region of the ribozyme to include a sequence that is complementary to the target HDAC1 and/or HDAC7 nucleic acid. Alternatively, an mRNA encoding a HDAC1 and/or HDAC7 may be used to select a catalytic RNA having a specific ribonuclease activity from a pool of RNA molecules. See, for example, Bartel & Szostak, Science 261:1411-1418 (1993).

In some aspects, the HDAC inhibitors of the present invention comprise a protein or polypeptide HDAC1 and/or HDAC7 and/or phosphorylated HDAC7 binding molecule. In some embodiments, the HDAC inhibitors of the present invention comprise a protein or polypeptide EMK and/or CTAK-1 and/or CaMK binding molecule. In some embodiments, the binding molecules bind directly and specifically to a target polypeptide e.g., HDAC1 and/or HDAC7 and/or phosphorylated HDAC7 and/or EMK and/or CTAK-1 and/or CaMK, and interfere with the enzymatic activity of the target polypeptide.

In some embodiments, the enzymatic activity of HDAC1 includes one or more activities selected from the group consisting of: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA.

In some embodiments, the enzymatic activity of HDAC7 and/or phosphorylated HDAC7 includes one or more activities selected from the group consisting of: deacetylation of lysine residues in the N-terminal tail of histones; deacetylation of lysine residues on the surfaces of nucleosome core; reduction of the transfer of acetyl moieties from lysine residues in the N-terminal tail of histones to Acetyl-CoA; reduction of covalent bonding between a serine amino acid residue on HDAC7 and a phosphoryl group; reduction in the amount of phosphorylated serine amino acid residues on HDAC7; dephosphorylation of existing phosphorylated serine amino acid residues on HDAC7; prevention of subsequent phosphorylation of serine amino acid residues on HDAC7 whether by direct inhibition of protein kinases e.g., EMK and/or CTAK-1 and/or CaMK, or direct activation of protein phosphatases e.g., PP2A phosphatase and/or myosin phosphatase, or by blocking the phosphorylation site by a binding molecule that directly binds to HDAC7; and combinations thereof.

Exemplary protein or polypeptide HDAC1 and/or HDAC7 and/or phosphorylated HDAC7 binding molecules preferably have little or no binding affinity for non-HDAC1 and/or non-HDAC7 and/or non-phosphorylated HDAC7 proteins.

In some embodiments, the HDAC inhibitors of the present invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. HDAC1 and/or HDAC7 and/or phosphorylated HDAC7 and/or EMK and/or CTAK1 and/or CaMK binding molecules may have both a heavy and a light chain. Preferred HDAC1 and/or HDAC7 and/or phosphorylated HDAC7 and/or EMK and/or CTAK1 and/or CaMK inhibitors of the present invention include, antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired activity, e.g., binding to HDAC1 and/or HDAC7 and/or phosphorylated HDAC7 and/or EMK and/or CTAK1 and/or CaMK polypeptides.

Anti-HDAC1 and/or anti-HDAC7 and/or anti-phosphorylated HDAC7 and/or anti-EMK and/or anti-CTAK1 and/or anti-CaMK antibodies can be produced using any of the commonly utilized methods for generating antibodies known to those in the art. Procedures for raising polyclonal antibodies are well known in the art. Typically, such antibodies are raised by immunizing an animal (e.g. a rabbit, rat, mouse, donkey, etc) by multiple subcutaneous or intraperitoneal injections of the relevant antigen (a purified HDAC1 and/or HDAC7 and/ or phosphorylated HDAC7 and/or EMK and/or CTAK1 and/ or CaMK peptide fragment, full-length recombinant HDAC1 and/or HDAC7 and/or EMK and/or CTAK1 and/or CaMK protein, fusion protein, etc) optionally conjugated to keyhole limpet hemocyanin (KLM), serum albumin, other immunogenic carrier, diluted in sterile saline and combined with an adjuvant (e.g. Complete or Incomplete Freund's Adjuvant) to form a stable emulsion. The polyclonal antibody is then recovered from blood or ascites of the immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc. Polyclonal antiserum can also be rendered monospecific using standard procedures (See e.g. Agaton et al., "Selective Enrichment of Monospecific Polyclonal Antibodies for Antibody-Based Proteomics Efforts," J Chromatography A 1043(1):33-40 (2004), which is hereby incorporated by reference in its entirety).

In some embodiments, monoclonal antibodies can be prepared using hybridoma methods, such as those described by Kohler and Milstein, "Continuous Cultures of Fused Cells Secreting Antibody of Predefined Specificity," Nature 256: 495-7 (1975), which is hereby incorporated by reference in its entirety. Using the hybridoma method, a mouse, hamster, or other appropriate host animal, is immunized to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against HDAC1 and/or HDAC7 and/or phosphorylated HDAC7, as determined by immunoprecipitation, immunoblotting, or by an in vitro binding assay such as radioimmunoassay (RIA) or enzyme-linked immunosorbent assay (ELISA) can then be propagated either in vitro culture using standard methods (James Goding, MONOCLONAL ANTIBODIES: PRINCIPLES AND PRACTICE (1986) which is hereby incorporated by reference in its entirety) or in vivo as ascites tumors in an animal. The monoclonal antibodies can then be purified from the culture medium or ascites fluid as described for polyclonal antibodies above.

In some embodiments, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, and monoclonal antibodies are generated by the host cells. Recombinant monoclonal antibodies or fragments thereof of the desired species can also be isolated from phage display libraries as described (McCafferty et al., "Phage Antibodies: Filamentous Phage Displaying Antibody Variable Domains," Nature 348:552-554 (1990); Clackson et al., "Making Antibody Fragments using Phage Display Libraries," Nature 352: 624-628 (1991); and Marks et al., "By-Passing immunization. Human Antibodies from V-Gene Libraries Displayed on Phage," J. Mol. Biol. 222:581-597 (1991), which are hereby incorporated by reference in their entirety).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In some embodiments, the monoclonal antibody against HDAC1 and/or HDAC7 and/or phosphorylated HDAC7 and/ or EMK and/or CTAK1 and/or CaMK is a humanized antibody. Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," Nature 321:522-525 (1986); Riechmann et al., "Reshaping Human Antibodies for Therapy," Nature 332:323-327 (1988); Verhoeyen et al., "Reshaping Human Antibodies: Grafting an Antilysozyme Activity," Science 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See e.g. Reisfeld et al., Monoclonal Antibodies and Cancer Therapy 77 (Alan R. Liss 1985) and U.S. Pat. No. 5,750,373 to Garrard, which are hereby incorporated by reference in their entirety). Also, the human antibody can be selected from a phage library, where that phage library expresses human antibodies (Vaughan et al., "Human Antibodies with Sub-Nanomolar Affinities Isolated from a Large Non-immunized Phage Display Library," Nature Biotechnology, 14:309-314 (1996); Sheets et al., "Efficient Construction of a Large Nonimmune Phage Antibody Library: The Production of High-Affinity Human Single-Chain Antibodies to Protein Antigens," Proc Nat'l Acad Sci USA 95:6157-6162 (1998); Hoogenboom et al., "By-passing Immunisation. Human Antibodies From Synthetic Repertoires of Germline VH Gene Segments Rearranged In Vitro," J Mol. Biol, 227:381-8 (1992); Marks et al., "By-passing Immunization. Human Antibodies from V-gene Libraries Displayed on Phage," J. Mol. Biol, 222:581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

In some embodiments, the HDAC inhibitors of the present invention include bispecific antibodies that specifically recognize HDAC1 and/or HDAC7 and/or phosphorylated HDAC7 and/or EMK and/or CTAK1 and/or CaMK. Bispecific antibodies are antibodies that are capable of specifically recognizing and binding at least two different epitopes. Bispecific antibodies can be intact antibodies or antibody fragments. Techniques for making bispecific antibodies are common in the art (Brennan et al., "Preparation of Bispecific Antibodies by Chemical Recombination of Monoclonal Immunoglobulin G1 Fragments," Science 229:81-3 (1985); Suresh et al, "Bispecific Monoclonal Antibodies From Hybrid Hybridomas," Methods in Enzymol. 121:210-28 (1986); Traunecker et al., "Bispecific Single Chain Molecules (Janusins) Target Cytotoxic Lymphocytes on HIV Infected Cells," EMBO J. 10:3655-3659 (1991); Shalaby et al., "Development of Humanized Bispecific Antibodies Reactive with Cytotoxic Lymphocytes and Tumor Cells Overexpressing the HER2 Protooncogene," J. Exp. Med. 175:217-225 (1992); Kostelny et al, "Formation of a Bispecific Antibody by the Use of Leucine Zippers," J. Immunol. 148: 1547-1553 (1992); Gruber et al., "Efficient Tumor Cell Lysis Mediated by a Bispecific Single Chain Antibody Expressed in *Escherichia coli*," J. Immunol. 152:5368-74 (1994); and U.S. Pat. No. 5,731,168 to Carter et al., which are hereby incorporated by reference in their entirety).

In certain embodiments, it may be desirable to use an antibody fragment, rather than an intact antibody, to increase tumor penetration. Various techniques are known for the production of antibody fragments. Traditionally, these fragments are derived via proteolytic digestion of intact antibodies (e.g. Morimoto et al., "Single-step Purification of F(ab')2 Fragments of Mouse Monoclonal Antibodies (immunoglobulins G1) by Hydrophobic Interaction High Performance Liquid Chromatography Using TSKgel Phenyl-5PW," Journal of Biochemical and Biophysical Methods 24:107-117 (1992) and Brennan et al., "Preparation of Bispecific Antibodies by Chemical Recombination of Monoclonal Immunoglobulin G1 Fragments," Science 229:81-3 (1985), which are hereby incorporated by reference in their entirety). However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870 to Rinderknecht et al., which is hereby incorporated by reference, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further encompasses variants and equivalents which are substantially homologous to the chimeric, humanized and human antibodies, or antibody fragments thereof. These can contain, for example, conservative substitution mutations, i.e. the substitution of one or more amino acids by similar amino acids, which maintain or improve the binding activity of the antibody or antibody fragment.

In some embodiments, HDAC inhibitors of the present invention include antibody mimics. A number of antibody mimics are known in the art including, without limitation, those known as monobodies, which are derived from the tenth human fibronectin type III domain (.sup.10Fn3) (Koide et al., "The Fibronectin Type III Domain as a Scaffold for Novel Binding Proteins," J. Mol. Biol. 284:1141-1151 (1998); Koide et al., "Probing Protein Conformational Changes in Living Cells by Using Designer Binding Proteins: Application to the Estrogen Receptor," Proc. Nat'l Acad. Sci. USA 99:1253-1258 (2002), which are hereby incorporated by reference in their entirety); and those known as affibodies, which are derived from the stable .alpha.-helical bacterial receptor domain Z of staphylococcal protein A (Nord et al., "Binding Proteins Selected from Combinatorial Libraries of an a-Helical Bacterial Receptor Domain," Nat. Biotechnol. 15(8): 772-777 (1997), which is hereby incorporated by reference in its entirety). Variations in these antibody mimics can be created by substituting one or more domains of these polypeptides with a HDAC1 and/or HDAC7 and/or phosphorylated HDAC7 and/or EMK and/or CTAK1 and/or CaMK specific domain and then screening the modified monobodies or affibodies for specificity for binding to HDAC1 and/or HDAC7 and/or phosphorylated HDAC7 and/or EMK and/or CTAK1 and/or CaMK.

In some embodiments, HDAC inhibitors of the present invention include HDAC1 and/or HDAC7 and/or phosphorylated HDAC7 and/or EMK and/or CTAK1 and/or CaMK binding oligopeptides. An HDAC1 and/or HDAC7 and/or phosphorylated HDAC7 and/or EMK and/or CTAK1 and/or CaMK-binding oligopeptide is an oligopeptide that binds, preferably specifically to the HDAC1 and/or HDAC7 and/or phosphorylated HDAC7 and/or EMK and/or CTAK1 and/or CaMK protein. Such oligopeptides may be chemically synthesized using known oligopeptide synthesis methodology or may be prepared and purified using recombinant technology.

Such oligopeptides are usually at least about 5 amino acids in length, but can be anywhere from 5 to 100 amino acids in length. Such oligopeptides may be identified without undue experimentation using well known techniques. Techniques for screening oligopeptide libraries for oligopeptides that are capable of specifically binding to a polypeptide target, in this case CD24, are well known in the art (see e.g. U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO84/03506 to Geysen and WO84/03564 Geysen, which are hereby incorporated by reference in their entirety).

In some embodiments, an HDAC inhibitor of the present invention is administered in combination with a cancer therapeutic agent. In some embodiments, the HDAC inhibitor of the present invention is administered to a patient undergoing conventional chemotherapy and/or radiotherapy e.g., to inhibit the proliferation of, or to eliminate the tumor stem cells remaining after receiving the conventional cancer therapy. In some embodiments, the cancer therapeutic agent is a chemotherapeutic agent. In some embodiments, the cancer therapeutic agent is an immunotherapeutic agent. In some embodiments, the cancer therapeutic agent is a radiotherapeutic agent.

In certain embodiments, an HDAC inhibitor of the present invention is linked or conjugated to a cancer therapeutic agent to facilitate direct delivery of the therapeutic agent to the solid tumor e.g., breast, ovarian, colon, etc. In an embodiment, the HDAC inhibitor is an antibody that is linked or conjugated to a cancer therapeutic. Methods of making such conjugates, in particular antibody-drug conjugates, are known in the art and are described in WO2005/077090 to Duffy et al., WO2005/082023 to Feng, WO2005/084390 to Alley et al., WO2006/065533 to McDonagh et al., WO2007/103288 to McDonagh et al., WO2007/011968 to Jeffery and WO2008/070593 to McDonagh et al., which are all hereby incorporated by reference in their entirety. Cancer therapeutics that can be linked to the HDAC inhibitor include, but are not limited to, chemotherapeutic agents or immunotherapeutic agents.

Exemplary chemotherapeutic agents include the toxins, diphtheria, ricin, and cholera toxin. Other chemotherapeutic agents that can be linked to the HDAC inhibitors of the present invention include alkylating agents (e.g. cisplatin, carboplatin, oxaloplatin, mechlorethamine, cyclophosphamide, chorambucil, nitrosureas); anti-metabolites (e.g. methotrexate, pemetrexed, 6-mercaptopurine, dacarbazine, fludarabine, 5-fluorouracil, arabinosycytosine, capecitabine, gemcitabine, decitabine); plant alkaloids and terpenoids including vinca alkaloids (e.g. vincristine, vinblastine, vinorelbine), podophyllotoxin (e.g. etoposide, teniposide), taxanes (e.g. paclitaxel, docetaxel); topoisomerase inhibitors (e.g. notecan, topotecan, amasacrine, etoposide phosphate); antitumor antibiotics (dactinomycin, doxorubicin, epirubicin, and bleomycin); ribonucleotides reductase inhibitors; antimicrotubules agents; and retinoids.

In some embodiments, the HDAC inhibitors of the present invention are linked to an immunotherapeutic agent. The immunotherapeutic agent can be a cytokine. The cytokine is exemplified by interleukin-1 (IL-1), IL-2, IL-4, IL-5, IL-β, IL-7, IL-10, IL-12, IL-15, IL-18, CSF-GM, CSF-G, IFN-γ, IFN-α, TNF, TGF-β but not always limited thereto.

In some embodiments, the HDAC inhibitors of the present invention can be linked or conjugated to a delivery vehicle containing a cancer therapeutic. Suitable delivery vehicles include liposomes (Hughes et al., "Monoclonal Antibody Targeting of Liposomes to Mouse Lung In Vivo," Cancer Res 49(22):6214-20 (1989), which is hereby incorporated by reference in its entirety), nanoparticles (Farokhzad et al., "Targeted Nanoparticle-Aptamer Bioconjugates for Cancer Chemotherapy In Viva," Proc Nat'l Acad Sci USA 103(16):6315-20 (2006), which is hereby incorporated by reference in its entirety), biodegradable microspheres, microparticles, and collagen minipellets. The delivery vehicle can contain any of the chemotherapeutic, radiotherapeutic, or immunotherapeutic agents described supra.

In one embodiment, the HDAC inhibitors of the present invention are conjugated to a liposome delivery vehicle (Sofou & Sgouros, "Antibody-Targeted Liposomes in Cancer Therapy and Imaging," Exp Opin Drug Deliv 5(2):189-204 (2008), which is hereby incorporated by reference in its entirety). Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug (cancer therapeutic) at the primary solid tumor site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," Proc. Nat'l Acad. Sci. USA 84:7851-5 (1987), which is hereby incorporated by reference in its entirety). When liposomes are endocytosed by a target cell, for example, they can be routed to acidic endosomes which will destabilize the liposome and result in drug release. Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery, The same problem exists for pH-sensitive liposomes in that as soon as the liposome vesicle comes into contact with a target cell, it will be engulfed and a drop in pH will lead to drug release.

Different types of liposomes can be prepared according to Bangham et al., "Diffusion of Univalent Ions Across the Lamellae of Swollen Phospholipids," J. Mol. Biol. 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

These liposomes can be produced such that they contain, in addition to the therapeutic agents of the present invention, other therapeutic agents, such as immunotherapeutic cytokines, which would then be released at the target site (e.g., Wolff et al., "The Use of Monoclonal Anti-Thy1 IgG1 for the Targeting of Liposomes to AKR-A Cells in Vitro and in Vivo," Biochim. Biophys. Acta 802:259-73 (1984), which is hereby incorporated by reference in its entirety).

In accordance with the methods of the present invention, administering to a subject having a solid tumor the HDAC inhibitor alone, in combination with a cancer therapeutic agent, linked to a cancer therapeutic agent, or conjugated to a delivery vehicle containing a cancer therapeutic, causes inhibition of tumor stem cell proliferation, a reduction in the number of tumor cells, elimination of tumor stem cells, a reduction in tumor growth, and a reduction in tumor size or bulk. In one embodiment, administration of the HDAC inhibitor diminishes tumor invasion and migration (i.e. tumor metastasis) thereby delaying or inhibiting tumor progression. Administration of the HDAC inhibitor alone, in combination with a cancer therapeutic agent or linked to a cancer therapeutic agent alleviates one or more of the symptoms associated with the solid tumor and reduces or prevents morbidity and mortality of the subject having the solid tumor.

In accordance with the methods of the present invention, administering to a subject having a hematological tumor the HDAC inhibitor alone, in combination with a cancer therapeutic agent, linked to a cancer therapeutic agent, or conjugated to a delivery vehicle containing a cancer therapeutic, causes inhibition of tumor stem cell proliferation, a reduction in the number of tumor cells, elimination of tumor stem cells, a reduction in tumor growth, and a reduction in tumor size or bulk. In one embodiment, administration of the HDAC inhibitor diminishes tumor invasion and migration (i.e. tumor metastasis) thereby delaying or inhibiting tumor progression. Administration of the HDAC inhibitor alone, in combination with a cancer therapeutic agent or linked to a cancer therapeutic agent alleviates one or more of the symptoms associated with the hematological tumor and reduces or prevents morbidity and mortality of the subject having the solid tumor.

In some aspects, the present invention provides pharmaceutical compositions comprising the HDAC inhibitor alone, the HDAC inhibitor in combination with a cancer therapeutic agent, or the HDAC inhibitor conjugated to a cancer therapeutic agent, and/or the HDAC inhibitor component linked to a delivery vehicle, which are suitable for treating a solid tumor. In some embodiments, the present invention provides pharmaceutical compositions comprising the HDAC inhibitor alone, the HDAC inhibitor in combination with a cancer therapeutic agent, or the HDAC inhibitor conjugated to a cancer therapeutic agent, and/or the HDAC inhibitor component linked to a delivery vehicle, which are suitable for treating a hematological tumor. Therapeutic formulations of the HDAC inhibitors (e.g. HDAC1 and/or HDAC7 and/or phosphorylated HDAC7 antibodies or antibody fragments, binding oligopeptides, HDAC1 and/or HDAC7 RNAi or antisense molecules, and HDAC1 and/or HDAC7 and/or phosphorylated HDAC7 binding small molecules) are prepared for storage by mixing the antibody, oligopeptide, nucleic acid or small molecule having the desired degree of purity with optional pharmaceutically acceptable carriers, excipients or stabilizers (REMINGTON'S PHARMACEUTICAL SCIENCES (A. Osol ed. 1980), which is hereby incorporated by reference in its entirety), in the form of lyophilized formulations or aqueous solutions. Acceptable carriers, excipients, or stabilizers are nontoxic to recipients at the dosages and concentrations employed, and include buffers such as acetate, Tris-phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS™ or polyethylene glycol (PEG).

The active therapeutic ingredients of the pharmaceutical compositions (i.e. HDAC inhibitors alone or linked to a cancer therapeutic agent) can be entrapped in microcapsules prepared using coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in REMINGTON'S PHARMACEUTICAL SCIENCES (A. Osol ed. 1980), which is hereby incorporated by reference in its entirety. In some embodiments, the HDAC inhibitors of the present invention can be conjugated to the microcapsule delivery vehicle to target the delivery of the therapeutic agent to the site of the tumor. Sustained-release preparations may be prepared. Suitable examples of sustained-release preparations include semi-permeable matrices of solid hydrophobic polymers containing the antibody or polypeptide, which matrices are in the form of shaped articles, e.g., films or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The therapeutically effective compositions containing the HDAC inhibitors of the present invention are administered to a subject, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes.

Other therapeutic regimens may be combined with the administration of the HDAC inhibitors. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In some embodiments, it may also be desirable to combine administration of the HDAC inhibitor with administration of an antibody directed against another tumor antigen associated with the solid tumor.

In another embodiment, the therapeutic treatment methods of the present invention involve the combined administration of one or more HDAC inhibitors, in combination with a cancer therapeutic agent, or conjugated to a distinct chemotherapeutic agent, radiotherapeutic agent, or immunotherapeutic agent, resulting in the administration of a cocktail of chemotherapeutic, radiotherapeutic, and/or immunotherapeutic agents. In another embodiment, the HDAC inhibitors alone or conjugated to the cancer therapeutic can be administered with one or more additional chemotherapeutic agents. Preparation and dosing schedules for such chemotherapeutic agents may be used according to manufacturers' instructions or as determined empirically by the skilled practitioner. Preparation and dosing schedules for such chemotherapy are also described in CHEMOTHERAPY SERVICE (M. C. Perry ed., 1992), which is hereby incorporated by reference in its entirety.

For the treatment of a solid tumor or a hematological tumor, the dosage and mode of administration will be chosen by the physician according to known criteria. A therapeutically effective dose of the HDAC inhibitor alone or linked to a cancer therapeutic agent is the amount effective for inhibiting the proliferation of tumor stem cells, reducing tumor cells e.g., killing tumor stem cells or non-stem tumor cells, reducing tumor size, reducing tumor cell migration and invasion, or reducing tumor growth. The dosage should not cause adverse side effects, such as unwanted cross-reactions, anaphylactic reactions, and the like. Generally, the dosage will vary with the age, condition, sex and route of administration, or whether other drugs are included in the regimen, and can be determined by one of skill in the art. The appropriate dosage of the HDAC inhibitor will also depend on the type of solid tumor (e.g., breast, ovarian, colon, brain, pancreatic, etc.) or hematological tumor (e.g., leukemia, myeloma, lymphoma, etc.) to be treated and the severity and course of the disease. The HDAC inhibitor may be appropriately administered to the patient at one time or over a series of treatments.

In some aspects, the present invention provides a method for treating a tumor that includes administering to an individual in need thereof an effective amount of an agent which specifically inhibits the activity or level of HDAC1 and/or HDAC7 and/or phosphorylated HDAC7 protein. In some embodiments, treating the tumor inhibits the proliferation of tumor stem cells and/or eliminates the tumor stem cells.

In some embodiments, the agent specifically inhibits the level and/or activity of EMK protein kinase. In some embodiments, the agent specifically inhibits the level and/or activity of CTAK-1 protein kinase. In some embodiments, the agent specifically inhibits the level and/or activity of CaMK protein kinase.

In some embodiments, the agent specifically increases the level and/or activity of PP2A phosphatase. In some embodiments, the agent specifically increases the level and/or activity of myosin phosphatase.

As discussed supra, examples of suitable agents that can be used for treating tumors include, but are not limited to nucleic acids e.g., antisense nucleic acids, oligopeptides, aptamers, ribozymes, small molecules, and antibodies or fragments thereof, and combinations thereof.

In some embodiments, the agent is administered with a pharmaceutically acceptable carrier. In some embodiments, the agent is co-administered with at least one additional chemotherapeutic agent, as described above.

In some embodiments, the agent includes interfering RNA targeted to HDAC1 and/or HDAC7 mRNA in the individual, which interferes with HDAC1 and/or HDAC7 expression within the individual, as described elsewhere herein. In certain embodiments, the interfering RNA is an siRNA. In certain embodiments, the interfering RNA is a small hairpin RNA.

In some embodiments, the agent includes an oligonucleotide having a nucleotide sequence that is complementary to HDAC1 and/or HDAC7 mRNA within the individual. In certain embodiments, the oligonucleotide is within the range of about 5 to about 50 nucleotides in length.

In some embodiments, the tumor is a solid tumor. In some embodiments, the solid tumor is one of a breast tumor, ovarian tumor, colon tumor, brain tumor, pancreatic tumor, prostate tumor, or lung tumor. In some embodiments, the tumor is a hematological tumor e.g., leukemia, myeloma, lymphoma, etc.

In some aspects, the invention provides a method for treating cancer that includes administering to an individual in need thereof an effective amount of an agent which specifically inhibits the activity or level of HDAC1 and/or HDAC7 and/or phosphorylated HDAC7. In some embodiments, the method of treating cancer is useful for inhibiting the proliferation of tumor stem cells. In some embodiments, the method of treating cancer is useful for eliminating tumor cells e.g., killing tumor stem cells.

In some embodiments, the cancer is characterized as one in which one or more cancerous cells produce an increased level and/or activity of HDAC1 and/or HDAC7 and/or phosphorylated HDAC7 protein. In certain embodiments, the cancerous cells are tumor stem cells. In certain embodiments, the tumor stem cells are breast tumor cells. In certain embodiments, the tumor stem cells are ovarian tumor cells. In certain embodiments, the tumor cells are colon tumor cells.

In some embodiments, the agent specifically inhibits the level or activity of EMK protein kinase. In some embodiments, the agent specifically inhibits the level or activity of CTAK-1 protein kinase. In some embodiments, the agent specifically inhibits the level and/or activity of CaMK protein kinase.

In some embodiments, the agent specifically increases the level and/or activity of PP2A phosphatase. In some embodiments, the agent specifically increases the level and/or activity of myosin phosphatase.

In some embodiments, the agent specifically inhibits the activity or level of HDAC1 and/or HDAC7 and/or phosphorylated HDAC7 in a tumor stem cell.

In some embodiments, the agent is an agent which downregulates HDAC1 and/or HDAC7 and/or phosphorylated HDAC7 gene expression, inhibits HDAC1 and/or HDAC7 translation, inhibits HDAC1 and/or HDAC7 and/or phosphorylated HDAC7 protein activity, and/or reduces the level of HDAC1 and/or HDAC7 and/or phosphorylated HDAC7 protein. HDAC1 and/or HDAC7 and/or phosphorylated HDAC7 activity includes one or more activities associated with the HDAC1 and/or HDAC7 and/or phosphorylated HDAC7 protein, including, but not limited to deacetylation of lysine residues in the N-terminal tail of histones, deacetylation of lysine residues on the surfaces of nucleosome core, reduction of the transfer of acetyl moieties from lysine residues in the N-terminal tail of histones to Acetyl-CoA, phosphorylation of a serine amino acid residue on HDAC7 and combinations thereof. In some embodiments, the HDAC7 activity includes the reduction of covalent bonding between a serine amino acid residue on HDAC7 and a phosphoryl group, the reduction in the amount of phosphorylated serine amino acid residues on HDAC7, the dephosphorylation of existing phosphorylated serine amino acid residues on HDAC7, the prevention of subsequent phosphorylation of serine amino acid residues on HDAC7 whether by direct inhibition of protein kinases or direct activation of protein phosphatases, or by blocking the phosphorylation site by a binding molecule that directly binds to HDAC7; and combinations thereof.

In some embodiments, the agent is an agent that inhibits transcription of HDAC1 and/or HDAC7 mRNA, degrades HDAC1 and/or HDAC7 mRNA, inhibits translation of HDAC1 mRNA, and combinations thereof. In an embodiment, the agent that inhibits transcription of HDAC1 and/or HDAC7 mRNA is an interfering RNA (RNAi). In an embodiment, the agent that degrades HDAC1 and/or HDAC7 mRNA comprises an interfering RNA (RNAi). In an embodiment, the agent that inhibits translation of HDAC1 and/or HDAC7 mRNA includes an antisense nucleic acids, a ribozyme, and combinations thereof as discussed in detail above. In an embodiment, the agent that inhibits HDAC1 and/or HDAC7 activity is an siRNA targeted to HDAC1 and/or HDAC7. In an embodiment, the agent that downregulates HDAC1 and/or HDAC7 expression comprises a small molecule inhibitor of HDAC1 and/or HDAC7. In an embodiment, the agent that downregulates HDAC1 and/or HDAC7 expression is an siRNA or pharmacologic agent capable of inhibiting HDAC1 and/or HDAC7 gene expression.

III. Methods for Generating Tumor Stem Cells

In some aspects, the present invention provides a method for generating tumor stem cells in vitro. In some embodiments, the method for generating tumor stem cells comprises overexpressing the level and/or activity of HDAC1 protein and HDAC7 protein in a cell, wherein the overexpression of both HDAC1 and HDAC7 protein in the cell transforms the cell into a tumor stem cell. In some embodiments, the method for generating tumor stem cells comprises overexpressing the level and/or activity of HDAC1 and phosphorylated HDAC7 protein in a cell, wherein the overexpression of both HDAC1 and phosphorylated HDAC7 protein in the cell transforms the cell into a tumor stem cell. In some embodiments, overexpression of phosphorylated HDAC7 includes overexpressing one or more protein kinases involved in phosphorylating HDAC7 e.g., EMK protein kinase, C-TAK1 protein kinase, and/or CAMK protein kinase. In some embodiments, overexpression of phosphorylated HDAC7 includes downregulating expression of one or more protein phosphatases involved in dephosphorylated HDAC7 e.g., PP2A phosphatase and/or myosin phosphatase Expression systems for controlling the expression levels of target proteins are well known in the art e.g., E. coli plasmid expression vectors. Any suitable expression system can be used e.g., cell-based or cell free, according to well known methods.

IV. Methods of Identifying Tumor Stem Cells

The invention provides methods of screening a biological sample from an individual for the presence of increased levels or activity of HDAC1, and/or HDAC7, and/or phosphorylated HDAC7 protein relative to standard levels or activity of HDAC1, and/or HDAC7, and/or phosphorylated HDAC7 protein. Such methods can be used for detecting and/or identifying the presence of tumor stem cells e.g., for the diagnosis and/or prognosis of proliferative disorders. Further provided are methods for treating individuals who are identified as having increased levels or activity of HDAC1, and/or HDAC7, and/or phosphorylated HDAC7 protein.

Methods of measuring the levels or activity of HDAC1, and/or HDAC7, and/or phosphorylated HDAC7 protein in cells are known in the art, including, but not limited to PCR, RT-PCR, ELISA, Western Blots, hybridization, mass spectrometry, etc. Standard molecular biology techniques are contemplated for precisely determining the expression level of HDAC1, and/or HDAC7, and/or phosphorylated HDAC7 protein in the cells of a given individual.

In some embodiments, a level and/or an activity and/or expression of a translation product of the gene coding for HDAC1 and/or HDAC7 protein and/or of a fragment, or derivative, or variant of said translation product, and/or the level of activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Antibodies directed at HDAC1, and/or HDAC7, and/or phosphorylated HDAC7 protein can be useful in measuring the level of HDAC1, and/or HDAC7, and/or phosphorylated HDAC7 protein expression e.g., protein levels or activity, in a given sample. Accordingly, the invention provides various immunological assays useful for the detection and quantification of HDAC1, and/or HDAC7, and/or phosphorylated HDAC7 proteins and polypeptides. Such assays generally comprise one or more HDAC1, and/or HDAC7, and/or phosphorylated HDAC7 directed antibodies capable of recognizing and binding a HDAC1, and/or HDAC7, and/or phosphorylated HDAC7 protein, as appropriate, and can be performed within various immunological assay formats well known in the art, including, for example, various types of radioimmunoassays, enzyme-linked immunosorbent assays (ELISA), enzyme-linked immunofluorescent assays (ELIFA), and the like. In addition, immunological imaging methods capable of detecting tumor stem cells are also provided by the invention including, for example, imaging methods using labeled HDAC1, and/or HDAC7, and/or phosphorylated HDAC7 antibodies. Such assays can be used clinically in the detection, monitoring, and prognosis of diseases associated with tumor stem cells (e.g., breast cancer, ovarian cancer, colon cancer, brain cancer, pancreatic cancer, prostate cancer, lung cancer, melanoma etc.).

In some embodiments, the level and/or activity of HDAC1, and/or HDAC7, and/or phosphorylated HDAC7 protein can be used as diagnostic markers for disease states e.g., the presence of tumor stell cells e.g., a cell proliferative disorder. The level and/or activity of HDAC1, and/or HDAC7, and/or phosphorylated HDAC7 protein in patient samples can be analyzed by a variety protocols that are well known in the art including the following non-limiting types of assays: PCR-free genotyping methods, Single-step homogeneous methods, Homogeneous detection with fluorescence polarization, Pyrosequencing, "Tag" based DNA chip system, Bead-based methods, fluorescent dye chemistry, Mass spectrometry based genotyping assays, TaqMan genotype assays, Invader genotype assays, microfluidic genotype assays, immunohistochemical analysis, the variety of Northern blotting techniques including in situ hybridization, RT-PCR analysis (for example on laser capture micro-dissected samples), western blot analysis, tissue array analysis, and any other methods known in the art or described elsewhere herein. Probes and primers can be designed so as to be specific to the HDAC1 and/or HDAC7 sequence, segments and complementary sequences thereof.

In some aspects, methods for identifying tumor stem cells are provided. In some embodiments, a method for identifying a tumor stem cell comprises detecting the presence of increased levels of HDAC1, and/or HDAC7 and/or phosphorylated HDAC7 protein in a sample containing cells.

In some embodiments, the increased level of HDAC1 protein in the sample compared to a standard level of HDAC1 protein indicates that the sample contains tumor stem cells. In some embodiments, the increased level of HDAC7 protein in the sample compared to a standard level of HDAC7 protein indicates that the sample contains tumor stem cells. In some embodiments, the increased level of phosphorylated HDAC7 protein in the sample compared to a standard level of phosphorylated HDAC7 protein indicates that the sample contains tumor stem cells. In some embodiments, the increased level of both HDAC1 and HDAC7 and/or phosphorylated HDAC7 protein in the sample compared to a standard level of HDAC1 and HDAC7 and/or phosphorylated HDAC7 protein indicates that the sample contains tumor stem cells.

In some embodiments, a method for identifying tumor stem cells is provided, the method comprising measuring in a cell the level or activity of HDAC1, and/or HDAC7 and/or phosphorylated HDAC7 protein and comparing the result of the measurement to a control measurement, wherein an increased level or activity of HDAC1, and/or HDAC7 and/or phosphorylated HDAC7 protein within the cell indicates that the cell is a tumor stem cell.

In some embodiments, the control measurement comprises measuring the level or activity of HDAC1, and/or HDAC7 and/or phosphorylated HDAC7 protein in a normal cell. In some embodiments, the control measurement comprises measuring the level of a standard cell that expresses HDAC1, and/or HDAC7 and/or phosphorylated HDAC7 protein at standard levels.

In some embodiments, the level and/or activity of HDAC1, and/or HDAC7 and/or phosphorylated HDAC7 protein is considered increased when the level or activity is observed to increase to any detectable degree e.g., an increase of 1%, 5%, 10%, 50%, 75%, 100%, 150%, 200%, 300%, 400%, or up to 500% or more. In some embodiments, the level and/or activity of HDAC1, and/or HDAC7 and/or phosphorylated HDAC7 protein is considered increased when the level and/or activity of HDAC1, HDAC7, and/or phosphorylated HDAC7 protein that is at least about 1, 2, 3, 4, 5, 6, 7, 8, 9, 10 fold or more higher than a reference or normal level or activity of HDAC1, HDAC7, and/or phosphorylated HDAC7 protein. In certain embodiments, the level and/or activity of HDAC1, and/or HDAC7 and/or phosphorylated HDAC7 protein is considered increased when the level or activity is about 0.1, 0.2, 0.3, 0.4, 0.5, 0.6, 0.7, 0.8, 0.9 fold higher than a reference or normal level or activity of HDAC1, and/or HDAC7 and/or phosphorylated HDAC7 protein.

In some embodiments, the cells in the sample comprise breast cells. In some embodiments, the cells in the sample comprise colon cells. In some embodiments, the cells in the sample comprise ovarian cells. In some embodiments, the cells in the sample comprise brain cells. In some embodiments, the cells in the sample comprise pancreatic cells. In some embodiments, the cells in the sample comprise prostate cells. In some embodiments, the cells in the sample comprise lung cells. In some embodiments, the cells in the sample comprise cells extracted from a solid tumor. In some embodiments, the cells in the sample comprise cells extracted from a hematological tumor. In some embodiments, the cells are cells obtained from a human subject.

V. Kits and Articles of Manufacture for Targeting Tumor Stem Cells

Kits and articles of manufacture of the present invention include an HDAC inhibitor of the present invention identified according to the methods discussed herein, e.g., combined with a pharmaceutically acceptable carrier, in a pharmaceutical formulation, e.g., in a pharmaceutical dosage form such as a pill, a powder, an injectable liquid, a tablet, dispersible granules, a capsule, a cachet or a suppository; optionally in association with a further therapeutic agent, e.g., as discussed herein. See for example, Gilman et al. (eds.) (1990), The Pharmacological Bases of Therapeutics, $8^{th}$ Ed., Pergamon Press; and Remington's Pharmaceutical Sciences, supra, Easton, Pa.; Avis et al. (eds.) (1993) Pharmaceutical Dosage Forms: Parenteral Medications Dekker, New York; Lieberman et al. (eds.) (1990) Pharmaceutical Dosage Forms: Tablets Dekker, New York; and Lieberman et al. (eds.) (1990), Pharmaceutical Dosage Forms: Disperse Systems Dekker, New York.

The kits and articles of manufacture of the present invention may also include information, for example, in the form of a package insert or label indicating that the HDAC inhibitor is intended to be administered to patients or having a tumor or malignancy which has been determined to comprise tumor stem cells by use of a method of detecting stem cells as discussed herein. The insert or label may take any form, such as paper or on electronic media such as a magnetically recorded medium (e.g., floppy disk) or a CD-ROM.

The label or insert may also include other information concerning the pharmaceutical compositions and dosage forms in the kit or article of manufacture. Generally, such information aids patients and physicians in using the enclosed pharmaceutical compositions and dosage forms effectively and safely. For example, the following information regarding the HDAC inhibitor may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

In some embodiments, the invention provides an article of manufacture comprising, packaged together, a specific inhibitor of HDAC1 or a pharmaceutical composition thereof comprising a pharmaceutically acceptable carrier; and a label stating that the inhibitor or pharmaceutical composition is indicated for treating patients having a tumor comprising tumor stem cells that exhibit increased HDAC1 protein levels.

In some embodiments, the invention provides an article of manufacture comprising, packaged together, a specific inhibitor of HDAC7 or a pharmaceutical composition thereof comprising a pharmaceutically acceptable carrier; and a label stating that the inhibitor or pharmaceutical composition is indicated for treating patients having a tumor comprising tumor stem cells that exhibit increased HDAC7 protein levels.

In some embodiments, the invention provides an article of manufacture comprising, packaged together, a specific inhibitor of phosphorylated HDAC7 or a pharmaceutical composition thereof comprising a pharmaceutically acceptable carrier; and a label stating that the inhibitor or pharmaceutical composition is indicated for treating patients having a tumor comprising tumor stem cells that exhibit increased phosphorylated HDAC7 protein levels.

In some embodiments, the invention provides an article of manufacture comprising, packaged together, a specific inhibitor of HDAC1 inhibitor and a specific inhibitor of HDAC7 or a pharmaceutical composition thereof comprising a pharmaceutically acceptable carrier; and a label stating that the inhibitors or pharmaceutical composition is indicated for treating patients having a tumor comprising tumor stem cells that exhibit increased HDAC1 protein levels and increased HDAC7 protein levels.

In some embodiments, the invention provides an article of manufacture comprising, packaged together, a specific inhibitor of HDAC1 inhibitor and a specific inhibitor of phosphorylated HDAC7 or a pharmaceutical composition thereof comprising a pharmaceutically acceptable carrier; and a label stating that the inhibitors or pharmaceutical composition is indicated for treating patients having a tumor comprising tumor stem cells that exhibit increased HDAC1 protein levels and increased phosphorylated HDAC7 protein levels.

VI. Compounds and Methods for Identifying Compounds

The invention provides methods of identifying compounds that inhibit tumor stem cell proliferation and/or eliminate tumor stem cells. Further provided are compositions useful for performing the inventive methods. In some aspects, the invention provides a method of identifying a compound that inhibits tumor stem cell proliferation in vitro, the method comprising (a) providing a cell exhibiting increased levels or activity of HDAC1 and/or HDAC7 and/or phosphorylated HDAC7 protein; (b) contacting the cell with a test compound; (c) determining whether the test compound inhibits the levels or activity of HDAC1 and/or HDAC7 and/or phosphorylated HDAC7 protein. Such compounds may be useful, e.g., to inhibit cell proliferation, e.g., for treatment of disorders involving excessive proliferation, such as tumors. In some embodiments, a method is used to identify compounds that eliminate tumor stem cells. In some embodiments, a method is used to identify compounds that interfere with histone deacetylation. In some embodiments, a method is used to identify compounds that interfere with phosphorylation of an HDAC protein involved in the deacetylation of histones.

The invention further provides methods of identifying a candidate agent that inhibits HDAC1 and/or HDAC7 and/or phosphorylated HDAC7 expression or activity. Further provided are compositions useful for performing the inventive methods. In some aspects, the invention provides a method of identifying a candidate agent that inhibits HDAC1 and/or HDAC7 and/or phosphorylated HDAC7 expression or activity, the method comprising: (a) expressing HDAC1 and/or HDAC7 protein in a cell population; (b) contacting the cell population with the candidate agent; and (c) measuring the level of expression or activity of HDAC1 and/or HDAC7 and/or phosphorylated HDAC7; wherein a decrease in expression or activity of the HDAC1 and/or HDAC7 and/or phosphorylated HDAC7 protein relative to a control cell population not exposed to the candidate agent is indicative of HDAC1 and/or HDAC7 and/or phosphorylated HDAC7 inhibitory activity of the candidate agent. Compounds identified using an inventive method may be used, e.g., to decrease deacetylation of the N-terminal tails of histones or decrease deacetylation of histones on the nucleosome core, which could be used to treat disorders involving the proliferation of tumor stem cells, for example. In some embodiments, the candidate agents that inhibit the level and/or activity of HDAC1 and/or HDAC7 and/or phosphorylated HDAC7 protein are useful for eliminating (e.g., killing) tumor stem cells.

The invention further provides methods of identifying compounds useful in the treatment and/or prevention of solid tumors. Further provided are compositions useful for performing the inventive methods. In some aspects, the invention provides a method of identifying compounds useful in the treatment and/or prevention of solid tumors and/or non-hematological tumors, the method comprising selecting compounds that reduce HDAC1 and/or HDAC7 and/or phosphorylated HDAC7 protein or activity in a cell, wherein the selected compounds that reduce HDAC1 and/or HDAC7 and/or phosphorylated HDAC7 protein or activity in the cell are useful for the treatment and/or prevention of solid tumors (e.g., breast, colon, ovarian, brain, pancreatic, lung, prostate, etc. . . . ) and/or non-hematological tumors, e.g., leukemias, myelomas, lymphomas, etc.

In some embodiments, the selecting step includes contacting the test compound with HDAC1 and/or HDAC7 and/or phosphorylated HDAC7 protein or with a cell exhibiting increased levels of HDAC1 and/or HDAC7 and/or phosphorylated HDAC7 protein. In some embodiments, the selecting step includes identifying compounds that inhibit HDAC1 and/or HDAC7 and/or phosphorylated HDAC7 activity. In some embodiments, the selecting step includes identifying compounds that reduce the expression of HDAC1 and/or HDAC7 in cells, e.g., antisense nucleic acids. Other examples of compounds suitable for reducing expression of HDAC1 and/or HDAC7 in cells include compounds that reduce the amount of HDAC1 and/or HDAC7 encoding transcripts in cells e.g., small interfering nucleic acids that induce RNA interference, such as small RNA hairpins, and the like; and compounds that reduce the amount of translation of HDAC1 and/or HDAC7 encoding transcripts in cells.

In some embodiments, the contacting step comprises identifying compounds that inhibit the enzymatic activity of HDAC1 and/or HDAC1 and/or phosphorylated HDAC7. Compounds that inhibit the enzymatic activity of HDAC1 and/or HDAC7 and/or phosphorylated HDAC7 can be identified by their ability to decrease the amount of histone deacetylation activity by the enzymatic removal of acetyl moieties from the lysine residues in the N-terminal tail of histones or by the enzymatic removal of acetyl moieties from the nucleosome core.

In some embodiments, the HDAC7 is phosphorylated. In some embodiments, HDAC7 is phosphorylated at a serine amino acid residue. In some embodiments, the serine amino acid residue of HDAC7 that is phosphorylated is serine-155, serine-178, serine-318, serine-344 or serine-479. Identifying compounds suitable for inhibiting the activity or level of phosphorylated HDAC7 protein includes screening for compounds that inhibit the activity or level of the phosphorylated HDAC7 protein itself, as well as compounds that inhibit the phosphorylation of HDAC7. Protein kinase EMK and/or protein kinase C-TAK1 and/or protein kinase CaMK are known to phosphorylated HDAC7. Accordingly, those of skill in the art will recognize how to adapt the methods for identifying compounds disclosed herein to identify compounds that inhibit protein kinase EMK and protein kinase C-TAK1, such as e.g., staurosporine, and protein kinase CaMK. In an embodiment, compounds are screened for their ability to stimulate or increase the level and/or activity of protein phosphatases known for dephosphorylating HDAC7. Protein phosphatase PP2A and myosin phosphatase are known for their ability to dephosphorylate HDAC7. Accordingly, those of skill in the art will recognize how to adapt the methods for identifying compounds disclosed herein to identify compounds that stimulate protein phosphatase PP2A and myosin phosphatase.

In some embodiments, a method for identifying compounds useful for the treatment of solid tumors includes screening pan-HDAC inhibitors for the ability to specifically inhibit the level and/or activity of HDAC1 and/or HDAC7 and/or phosphorylated HDAC7, the method comprising: a) providing a cell in which the level and/or activity of HDAC1 and/or HDAC7 and/or phosphorylated HDAC7 is increased compared to a reference level and/or activity of HDAC1 and/or HDAC7 and/or phosphorylated HDAC7; b) contacting the cell with a pan-HDAC inhibitor; and c) measuring the level and/or activity of HDAC1 and/or HDAC7 and/or phosphorylated HDAC7 in the cell, wherein the pan-HDAC inhibitors that decrease the level and/or activity of HDAC1 and/or HDAC7 and/or phosphorylated HDAC7 in the cell are useful for specifically inhibiting the level and/or activity of HDAC1 and/or HDAC7 and/or phosphorylated HDAC7. In some embodiments, the pan-HDAC inhibitors that inhibit the level and/or activity of HDAC1 and not the level and/or activity of HDAC7 and/or phosphorylated HDAC7 are useful for specifically inhibiting HDAC1. In some embodiments, the pan-HDAC inhibitors that inhibit the level and/or activity of HDAC7 and not the level and/or activity of HDAC1 and/or phosphorylated HDAC7 are useful for specifically inhibiting the level and/or activity HDAC7. In some embodiments, the pan-HDAC inhibitors that inhibit the level and/or activity of phosphorylated HDAC7 and not the level and/or activity of HDAC1 and/or HDAC7 are useful for specifically inhibiting the level and/or activity phosphorylated HDAC7.

In some embodiments, the method of screening pan-HDAC inhibitors for specific inhibitors of the level and/or activity of HDAC1, and/or HDAC7 and/or phosphorylated HDAC7 includes: a) providing a cell in which HDAC2, HDAC3, HDAC4, HDAC5, HDAC6, HDAC8, HDAC9, HDAC10 and HDAC11 are expressed at normal levels and in which HDAC1 and HDAC7 are expressed at increased levels compared to normal levels of expression; b) contacting the cell with a pan-HDAC inhibitor; c) measuring the levels and/or activity of HDAC1, HDAC2, HDAC3, HDAC4, HDAC5, HDAC6, HDAC7, HDAC8, HDAC9, HDAC10, and HDAC11; wherein the pan-HDAC inhibitors that decrease the level and/or activity of HDAC1 and/or HDAC7 and that do not significantly alter the level and/or activity of HDAC2, HDAC3, HDAC4, HDAC5, HDAC6, HDAC8, HDAC9, HDAC10 and HDAC11 are useful for specifically inhibiting HDAC1 and/or HDAC7. In some embodiments, the invention provides a method of screening pan-HDAC inhibitors for their ability to inhibit the proliferation of tumor stem cells, the method including a) providing a cell which exhibits increased levels and/or activity of HDAC1 and HDAC7 and/or phosphorylated HDAC7; b) contacting the cell with a pan-HDAC inhibitor; and c) determining whether the levels and/or activity of HDAC1 and HDAC7 and/or phosphorylated HDAC7 are decreased, wherein the pan-HDAC inhibitors that reduce the levels and/or activity of HDAC1 and HDAC7 and/or phosphorylated HDAC are useful for inhibiting the proliferation of and/or eliminating tumor stem cells.

In some embodiments, the pan-HDAC inhibitor is a Class I HDAC inhibitor. In some embodiments, the pan-HDAC inhibitor is a Class II HDAC inhibitor. In some embodiments, the pan-HDAC inhibitor is a Class I and Class II HDAC inhibitor. In some embodiments, the pan-HDAC inhibitor is one of a hydroxamic acid derived compound, a cyclic tetrapeptide, a short-chain fatty acid, a synthetic pyridyl carbamate derivative, a synthetic benzamide derivative, or a ketone.

In some embodiments, the hydroxamic acid derived compound includes one of trichostatin (TSA), suberoylanilide hydroxamic acid (SAHA), M-carboxycinnamic acid bis-hydroxamide (CBHA), azelaic bis-hydroxamic acid (ABHA), NVP-LAQ824, LBH589, oxamflatin, PXD101, scriptaid, or pyroxamide or analogues or derivatives thereof.

In some embodiments, the cyclic tetrapeptide includes one of depsipeptide (FK228, FR901228), apicidine, trapoxin, HC-toxin, chlamydocin, depudesin, or CHAPS or analogues or derivatives thereof.

In some embodiments, the short chain fatty acid includes one of valproic acid (VA), phenyl butyrate (PB), phenyl acetate (PA), sodium butyrate (SB), and AN-9 (Pivanex) or analogues or derivatives thereof.

In some embodiments, the synthetic pyridyl carbamate derivative includes MS-275 or an analogue or derivative thereof.

In some embodiments, the synthetic benzamide derivative includes CI-994 (N-acetyldinaline) or an analogue or derivative thereof.

In some embodiments, the ketone includes trifluoromethyl ketone, $\alpha$-ketomides, and analogues or derivatives thereof.

Compounds identified using an inventive method may be used for any purpose in which it is desired to alter expression or activity of the gene product. In some embodiments, a compound is useful for increasing or decreasing production of a functional gene product of interest by cells. In some embodiments, the cells are isolated cells. In some embodiments, a compound is useful for increasing or decreasing production of a gene product in vivo.

A compound identified using an inventive method, e.g., a compound identified as a modulator of a DNA or gene product of interest, can be tested in cell culture or in animal models ("in vivo") to further characterize its effects. Cytotoxicity can be assessed e.g., using any of a variety of assays for cell viability and/or proliferation such as a cell membrane integrity assay, a cellular ATP-based viability assay, a mitochondrial reductase activity assay, a BrdU, EdU, or H3-Thymidine incorporation assay, a DNA content assay using a nucleic acid dye, such as Hoechst Dye, DAPI, Actinomycin D, 7-aminoactinomycin D or propidium iodide, a cellular metabolism assay such as AlamarBlue, MTT, XTT, and CellTitre Glo, etc. The compound can be tested in an animal model of a disorder, e.g., a genetic disorder.

One of skill in the art would be aware of suitable methods to assess expression and/or activity of a gene product of interest. Methods known in the art can be used for measuring mRNA or protein. A variety of different hybridization-based or amplification-based methods are available to measure RNA. Examples include Northern blots, microarray (e.g., oligonucleotide or cDNA microarray), reverse transcription (RT)-PCR (e.g., quantitative RT-PCR), or reverse transcription followed by sequencing. The TaqMan® assay and the SYBR® Green PCR assay are commonly used real-time PCR techniques. Other assays include the Standardized (Sta) RT-PCRT™ (Gene Express, Inc., Toledo, Ohio) and QuantiGene® (Panomics, Inc., Fremont, Calif.). In some embodiments the level of mRNA is measured. In other embodiments, a reporter-based system is used. Assays for activity of a gene product (e.g., enzymatic activity, binding activity) would be selected base on the particular activity of interest. In general, assays could be cell-free or cell-based in various embodiments of the invention.

A wide variety of test compounds can be used in the inventive methods. For example, a test compound can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see https://mli.nih.gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, anti inflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or antihormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability. In some embodiments, a test compound is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays (some of which are mentioned above). In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

In some embodiments, a method of identifying compounds is performed using a high throughput screen (HTS). A high throughput screen can utilize cell-free or cell-based assays. High throughput screens often involve testing large numbers of compounds with high efficiency, e.g., in parallel. For example, tens or hundreds of thousands of compounds can be routinely screened in short periods of time, e.g, hours to days. Often such screening is performed in multiwell plates containing, e.g., e.g., 96, 384, 1536, 3456, or more wells (sometimes referred to as microwell or microtiter plates or dishes) or other vessels in which multiple physically separated cavities are present in a substrate. High throughput screens can involve use of automation, e.g., for liquid handling, imaging, data acquisition and processing, etc. Without limiting the invention in any way, certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening Methods and Protocols (Methods in Molecular Biology) by William P. Janzen (2002) and High-Throughput Screening in Drug Discovery (Methods and Principles in Medicinal Chemistry) (2006) by Jorg Hüser.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context.

The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Subpopulations of Isogenic Tumor Cells have Stem and Non-Stem Properties

Using a model pair of isogenic breast tumor cell lines, it was determined that subpopulations of isogenic tumor cells have stem and non-stem cell properties. To analyze differences between TSCs and non-stem tumor cells (non-STCs), two cell types BPLER and HMLER which are similar to TSCs and non-STCs, respectively were used. It was observed that the BPLER breast tumor cells formed tumors with as low as 5 unsorted cells per injection which is similar to that of Fluorescence-activated cell sorting (FACS) purified TSCs. HMLER cells, on the other than, were shown to be similar to non-STCs in that at least $10^{4-6}$ unsorted cells were required for tumor formation within these cells.

The results were replicated using additional pairs of cells and it was confirmed that BPLER cells are orders-of-magnitude more capable of initiating tumors than their isogenic HMLER pair (FIG. 1A). Similarly, BPLER cells demonstrated a higher tumorsphere forming capacity than HMLER cells in each of the three paired isogenic lines (FIG. 1B). Tumorsphere formation assays used to measure the frequency of TSCs in bulk cell populations correlated with the increased ability of BPLER cells to form tumors in vivo. These results are supported by the finding that the expression level of TSC-associated tumor cell markers CD166 and CD326 was increased in BPLER cells compared to HMLER cells (FIG. 1C). Further, BPLER and HMLER cells enriched with FACS employing CD166, CD326 and CD44 revealed subpopulations enriched in cells forming tumorspheres (FIG. 1D and FIG. 1F) and breast and ovarian tumor cells (FIG. 1F). Previous work of others has shown that these markers enrich for TSCs from primary human solid tumors and colon, breast, and ovary tumor cell lines. These results suggest that the typical markers and increased tumor initiation phenotype characteristic of well purified TSC subpopulations isolated using FACS are displayed by unsorted, bulk BPLER cultures.

Notably, it has been shown that tumor initiation efficiency differences between BPLER and HMLER cells were independent of medium conditions and genetic differences. Further, each of these BPLER/HMLER pairs were isolated from the same individual and transformed with oncogenes that were identical. Accordingly, the above model provides a well controlled setting for examination of the differences between TSCs and non-STCs without resorting to cell sorting.

Example 2

HDAC Inhibitor TSA Specifically Targets Tumor Stem Cells

Above a BPLER/HMLER model pair of isogenic breast tumor cell lines that provided a well controlled setting for evaluating the differences between TSCs and non-STCs was discussed. Using these BPLER/HMLER model pairs, the functionality of TSCs as a viable target for the treatment of human tumors was further evaluated. The response of these BPLER/HMLER pairs to the HDAC inhibitor trichostatin A (TSA) was assessed and we found that the HDAC inhibitor TSA specifically targets tumor stem cells. For example, the LD50 for TSA applied to TSC-like BPLER cells was an order-of-magnitude lower than the LD50 for TSA applied to the non-STC-like HMLER cells (FIG. 2A). When treated with conventional chemotherapeutics, however, BPLER and HMLER cell types showed similar sensitivity, namely the LD50 for paclitaxel and 5-fluorouracil did not differ between BPLER and HMLER cell types (FIG. 2A). Taken together, this data suggests that the class of non-selective HDAC inhibitors may exert an anti-proliferative effect preferentially on TSC-like BPLER cells as compared to non-STCs-like HMLER cells.

Figure 3:
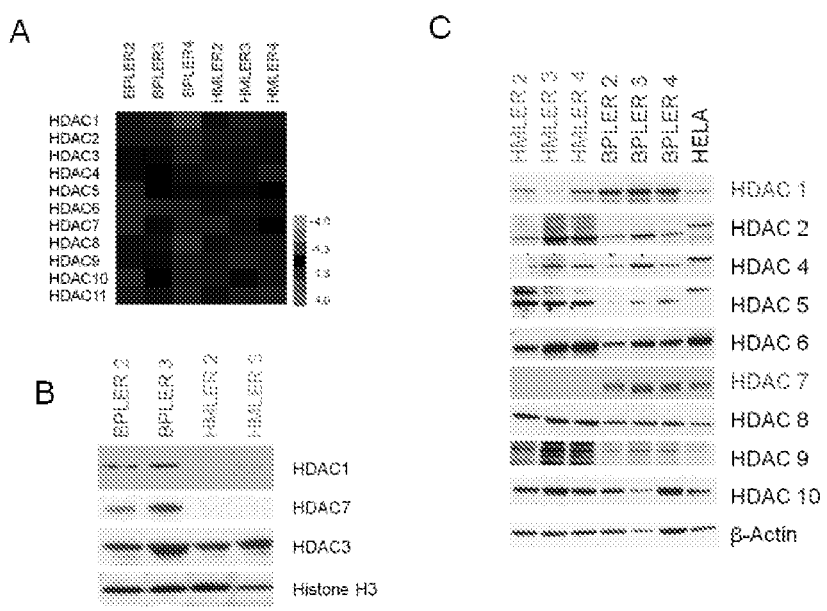
FIG. 3. HDAC1 and HDAC7 are highly expressed in tumor stem cells. A) Affymetrix HU-133 plus array showing that mRNA transcript levels of HDACs 1 through 11 do not differ significantly between BPLER and HMLER cells. B) Western blot of isogenic BPLER/HMLER cells showing that protein levels of HDAC1 and HDAC7 are significantly higher in TSC-like BPLER cells than in non-STC-like HMLER cells. C) Western blot of isogenic HMLER/BPLER cell extracts showing that the other nine HDAC proteins e.g., HDAC2, HDAC3, HDAC4, HDAC5, HDAC6, HDAC8, HDAC9 and HDAC10, are the same between the two cell types.

Unexpectedly, it was observed that even short-term TSA treatment significantly decreased BPLER cell capacity to form mammospheres, suggesting that TSA specifically targets the TSC phenotype of BPLER cells (FIG. 2B). In contrast, TSA did not affect HMLER cell capacity to form mammospheres. Nor was any difference observed between BPLER and HMLER cells with paclitaxel or 5-fluorouracil (FIG. 3B). As noted above, tumorsphere formation capacity correlates with TSC subpopulations. With the tumorsphere assay employed, a single tumor cell can form a multicellular tumorsphere in suspension. To assess the short term effect of drug treatment, drugs were removed after treating the tumor cells in routine 2D culture conditions for 24 hours, and after a recovery period of 24 hours tumorsphere cultures were suspended in a medium free of drugs for 7 days. Surprisingly, 24 hour short term treatment with the HDAC inhibitor affected the formation of tumorspheres for the 8 days following drug removal, indicating that the TSC phenotype was stably altered by TSA treatment. In contrast, treatment with 5-fluorouracil and paclitaxel had a cytotoxic effect on BPLER and HMLER cells only when the drugs were present, however, tumorsphere formation was not inhibited after removal of the drugs. Further, the BPLER and HMLER cells showed no difference in response to paclitaxel and 5-fluorouracil. These findings indicate that in contrast to the chemotherapeutics 5-fluorouracil and paclitaxel, which showed no preference for the BPLER TSC-like cells, the HDAC inhibitor TSA may be a specific inhibitor of the TSC phenotype.

Example 3

Tumor Stem Cells Possess Increased Levels of HDAC1 and HDAC7 Protein

Above it was demonstrated that TSA, a non-selective HDAC inhibitor, specifically inhibited the TSC phenotype by selectively inhibiting tumorsphere formation in TSC-like BPLER cells. To elucidate a specific TSC target of TSA, expression of HDACs in BPLER and HMLER cells was evaluated. Human cells contain 18 HDACs which are organized into four distinct classes (Class I through IV). Class I HDACs include HDAC1, HDAC2, HDAC3 and HDAC8. Class II HDACs include HDAC4, HDAC5, HDAC6, HDAC7, HDAC9 and HDAC10. Class III HDACs (members of the SIRT family of proteins) are NAD+ dependent deacetylases and therefore were not evaluated further. Class IV HDACs (HDAC11) are zinc-dependent enzymes. Class IV HDACs are the target of some HDAC inhibitors currently in clinical use. HDAC inhibiting drugs inhibit different subsets of the HDAC family. Some drugs, such as TSA, are known to inhibit both Class I and Class II HDACs in humans.

Significantly and unexpectedly, it was observed that although there is no significant difference between levels of mRNA transcripts for HDACs 1 through HDAC11 (FIG. 3A), HDAC1 and HDAC7 protein expression levels are significantly higher in BPLER cells than in HMLER cells (FIG. 3B). Notably, HDAC protein levels for the other nine HDAC proteins surveyed are similar for BPLER and HMLER cells (FIG. 3C). This data directed the experimental focus to HDAC1 and HDAC7 as potential TSC specific targets of TSA.

To confirm the experimental HDAC1 and HDAC7 expression data obtained using the BPLER/HMLER model pair, FACS enriched TSC subpopulations were evaluated in the breast cancer cell lines MCF-7, SUM-159 and MDA-MB-231 and it was observed that much higher levels of HDAC1 and HDAC7 protein were expressed in these TSC subpopulations (FIG. 4A). Consistent with these findings, higher global HDAC activity in TSC-enriched subpopulation breast, ovarian and colon tumor cell lines was observed, suggesting a correlation between TSCs and HDAC activity across different types of tumors. Taken together, increased expression of HDAC1 and HDAC7 protein in TSCs implicates HDAC1 and HDAC7 protein as markers for identifying tumor stem cells as well as therapeutic targets for the treatment of solid human tumors.

Example 4

HDAC1 and HDAC7 are Necessary for the TSC Phenotype

Figure 5:
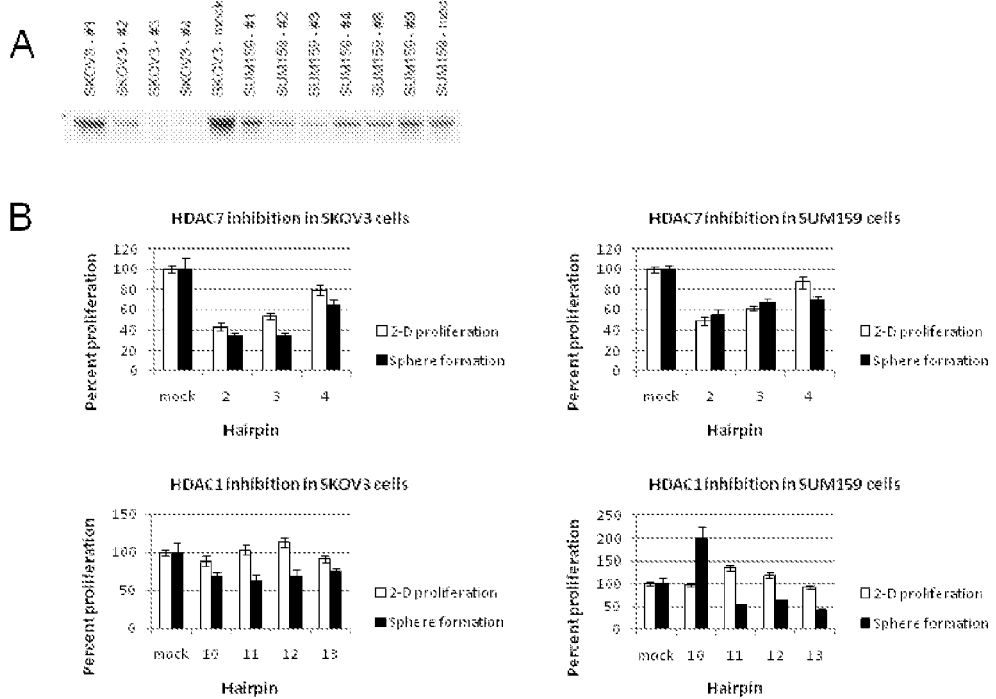
FIG. 5. HDAC1 and HDAC7 are necessary for the TSC phenotype. A) Image showing small RNA hairpins identified by western blot that significantly decreased expression of HDAC1 and HDAC7 proteins. B) Charts showing that inhibition of either HDAC1 or HDAC7 in cell culture and in tumor sphere assays resulted in decreased tumor sphere formation in ovarian cancer cells SKOV3 (left two panels) and breast cancer cells SUM159 (right two panels).
Figure 6:
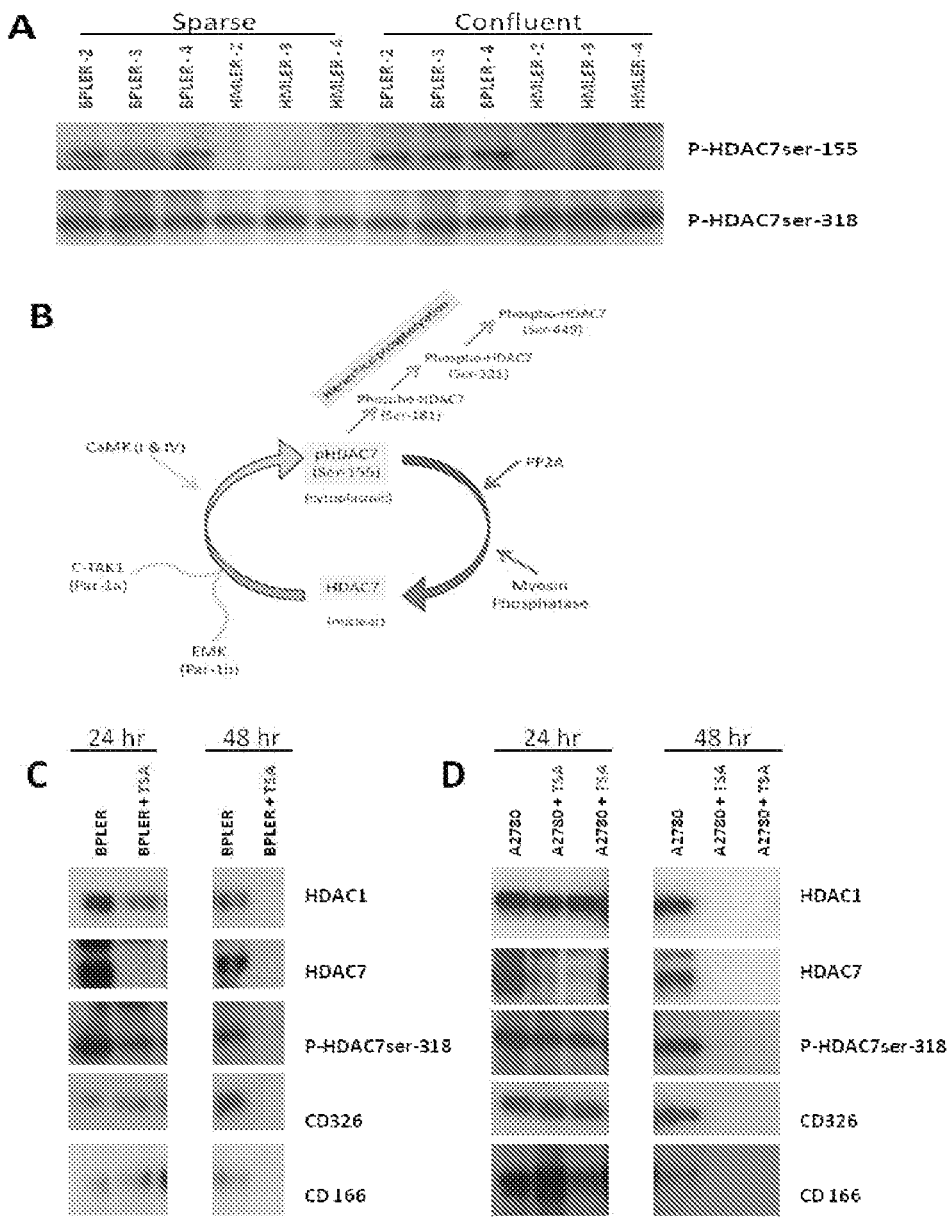
FIG. 6. Phospho-HDAC7 expression varies between the HMLER and BPLER cell lines at sparse as well as confluent densities, and is altered by HDAC inhibitor (TSA) treatment, A) Western Blot comparing the BPLER-2, BPLER-3, BPLER-4 and HMLER-2, HMLER-3, HMLER-4 cell lines for phosphorylated HDAC7 levels. Phospho-HDAC7ser-155, a modification involved in nuclear export, is present in all three BPLER cell lines and absent from all three HMLER cell lines. Density does not alter the levels of Phospho-HDAC7ser-155 in the BPLER lines. Phospho-HDAC7ser-318, a modification that enhances nuclear accumulation, but is not essential for nuclear export, is present in all HMLER and BPLER cell lines. Although density does not alter the levels of Phospho-HDAC7ser-318 in the BPLER lines, confluency increases levels present in the HMLER cell lines. B) Image showing that regulation of HDAC7ser-155 phosphorylation is modulated by the protein kinases, CaMK, c-TAK1 (Par-1a) and EMK (Par-1b), and the protein phosphatases PP2A and myosin phosphatase. c-TAK1 and EMK function in tandem to drive phosphorylation of ser-155, and this modification allows for the hierarchical phosphorylation of ser-181, ser-321 and ser-449 thus creating a binding site for 14-3-3. Phosphorylation by CaMK promotes 14-3-3 binding and nuclear export. PP2A and myosin phosphatase function to dephosphorylate this residue, thereby inhibiting 14-3-3 binding and driving nuclear localization of HDAC7. C) Western Blot showing that TSA treatment of the BPLER cell lines decreases the total protein levels of HDAC1 and HDAC7, and the levels of Phospho-HDAC7ser-318 by 24 hours, with significant down-regulation observable by 48 hours. The cancer stem cell markers CD326 and CD166 are down-regulated by TSA treatment at 48 hours. D) Western Blot showing that TSA treatment of the A2780 human ovarian cancer cell line decreases total protein levels of HDAC7 by 24 hours, with significant down-regulation of total HDAC1, HDAC7 levels and Phospho-HDAC7ser-318 observable by 48 hours. The cancer stem cell markers and CD166 are down-regulated by TSA treatment at 48 hours (Western Blots 15 ug whole cell lysate/lane).

Above it was shown that the TSC phenotype displays increased levels of HDAC1 and HDAC7 protein. To further evaluate the functional significance of HDAC1 and HDAC7 as markers and therapeutic targets for the TSC phenotype, it was evaluated whether increased expression of HDAC1 and HDAC7 protein was critical for maintaining the TSC phenotype. Small RNA hairpins were identified that substantially decreased HDAC1 and HDAC7 protein levels (FIG. 5A). Inhibiting HDAC1 or HDAC7 protein levels using these small RNA hairpins lead to decreased tumorsphere formation in breast cancer cells (BPLER and SUM159) and ovarian cancer cells (SKOV3) as measured by tumorsphere assays (FIG. 5B). The above results therefore suggest that HDAC1 and HDAC7 protein expression are required for the TSC phenotype.

Example 5

HDAC1 Activity More Intimately Involved in Stem Cell Proliferation than Non-Stem Cell Proliferation Inhibition of HDAC1 using siRNA vectors in tumor cell lines including breast, ovarian, and colon had a larger inhibitory impact on formation of tumorspheres when compared to routine proliferation in 2D culture. Decreased ES cell proliferation and death before embryonic day 10.5 in HDAC1-deficient mouse embryos has been reported. However, HDAC1 deletion in adult tissues had no impact on viability. These findings suggest that HDAC1 activity may be more intimately involved in stem cell proliferation than in the proliferation of other types of cells.

Example 6

TSA Treatment of Breast Tumor Cells Lead to a 10-Fold Decrease in HDAC7 Expression Levels It was observed that inhibition of HDAC7 protein decreased tumorsphere formation in breast, ovary, and colon tumor cell lines. However, in contrast to HDAC1 discussed above, differential effects on routine 2D cell proliferation were not as pronounced for HDAC7. Previous work of others has found that TSA treatment of breast tumor cells caused almost a 10-fold decrease on HDAC7 expression levels (Duong et al.) Notably, however, changes in expression of other Class I and Class II HDACs were minimal (less than 2-fold). Taken together, these findings suggest that HDAC7 may be more highly expressed in tumor cells and thus HDAC7 may be a marker and therapeutic target for the treatment of human tumors.

Example 7

Tumor Stem Cells Exhibit Specific Phospho-HDAC Expression

Above it was shown that TSC-like BPLER cells exhibit increased levels of expression of HDAC1 and HDAC7 protein which is required for the TSC phenotype. It was further observed that compared to non-stem like HMLER cells, TSC-like BPLER cells express higher levels of HDAC7 than is phosphorylated at serine-155. It was also observed that serine-318 was not differentially phosphorylated in BPLER and HMLER cells, suggesting that the differential phosphorylation of serine-155 is specific. Phosphorylation of HDAC7 at serine-155 initiates progressive phosphorylation of the ser-181, ser-321, and ser-449 on HDAC7 and results in nuclear to cytoplasmic translocation of HDAC7. However, ser-318 phosphorylation has not been associated with the intracellular translocation of HDAC7. Phosphorylation of HDAC7 is believed to be regulated by CAMK, TAK-1 and EMK, and dephosphorylation of HDAC7 is believed to be regulated by PP2A and myosin phosphatase. HDAC inhibitor trichostatin A (TSA) treatment of breast cancer cells (BPLER) and ovarian cancer cells (A2780) resulted in a dramatic reduction in HDAC1, HDAC7, phosphorylated HDAC7, and tumor stem cell markers CD326 and CD166 within 24 to 28 hours. These results reveal that tumor stem cells express high levels of phosphorylated forms of HDAC7. TSA reduced levels of HDAC1, HDAC7 and phosphorylated HDAC7. For these reasons, TSA could be an effective agent against tumor stem cells. However, TSA is a pan-HDAC inhibitor that inhibits the entire HDAC family of proteins. Furthermore, TSA becomes increasingly less specific and starts to inhibit many non-HDAC targets and activities at the high doses that would be required in the clinic. TSA's broad spectrum of activity causes side effects, leading to patient toxicity. However, derivatives of TSA or other small molecules that specifically inhibit HDAC1, HDAC7 and phosphorylated HDAC7 without the non-specific activities associated with TSA could be effective treatment against tumor stem cells.

Experimental Procedures Used in the Examples

Cell Culture

BPLER and HMLER cells were maintained in WIT-T (Stemgent) and MGEM (Lonza) medium at 37° C. and 5% $CO_2$. The remaining cell lines were grown in DMEM/F12 (Gibco) with 10% fetal bovine serum (FBS) at 37° C. and 5% $CO_2$. The BPLER cells were grown on Primaria plasticware (BD Biosciences). The remaining cells were grown on standard plasticware (Falcon). The mammospheres were maintained in a 1:1 ratio of WIT-T/MEGM (less bovine pituitary extract) using 2% B27 (Invitrogen), 20 ng/ml EGF, 20 ng/ml bFGF (BD Biosciences), 4 ug/ml heparin (Sigma), and 0.5% methyl cellulose. Sphere formation experiments were carried out by plating 15,000-20,000 cells/well into 6-well ultra-low attachment plates (Corning). The cells were fed at days 1, 3, and 5, and spheres were counted at day 7.

Drug Treatments

Drug treatment experiments were performed in a 1:1 ratio of WIT-T/MEGM media. The following drug compounds were prepared in DMSO: trichostatin A (Sigma Chemical); paclitaxel (Sigma Chemical); and 5-fluorouracil (Sigma Chemical). To evaluate the drug effect on 2D proliferation of BPLER and HMLER cells, the cells were plated at 125,000 cells/well in 6-well Primaria plates. Drug-containing media was added to each well after 24 hours. The cells were treated continuously for 4 days with drug-containing media changes each day. Cell number was counted with a hemocytometer after 4 days of treatment. To evaluate the drug effect on BPLER and HMLER cell mammosphere formation, cells were plated at 50% confluence in Primaria flasks. After 24 hours, drug-containing media was added to each flask. After 24 hours of treatment with the drug-containing media, the cells recovered for 24 hours in a drug-free media. Cells were then plated for the mammosphere protocol as described previously.

Flow Cytometry and Cell Sorting

Non-enzymatic cell dissociation buffer (Invitrogen, #13151-014) was used to harvest cells from sub-confluent culture plates, however, cells were never trypsinized to produce single cell suspensions for cell sorting. Cell pellets were washed and resuspended with HBSS buffer containing 0.2% BSA. Cells were stained with fluorophore-conjugated monoclonal antibodies according to the manufacturer's protocol. The following antibodies were used for cell sorting: anti-CD44, APC conjugated (BD Pharmingen, #559942); CD133/1, PE conjugated (Miltenyi biotech, #130-080-801); CD166, PE conjugated (BD Pharmingen, #559263); and CD326, PerCP-Cy5.5 conjugated (BD Pharmingen, #347199). An Accuri C6 cytometer (Accuri cytometers Inc., Ann Arbor, Mich.) was used to perform flow cytometry. The sorted cells were collected in heat-inactivated fetal serum or HBSS buffer containing 2% BSA. The purity of the sorted cells ranged between 90-95%.

Soft Agar Colony Formation

To assay soft agar colony formation, cells were harvested using 0.25% trypsin or non-enzymatic cell dissociation buffer (Invitrogen, #13151014), sorted by flow cytometry according to cell surface markers CD166, CD326 and CD44, and live cells were counted using trypan blue exclusion. A six-well cell culture plate was coated with 1-2 mL media containing 0.6% Difco Agar Noble (BD, #214230), and overlaid with cells suspended in 2.5 mL media containing 0.4% Difco Agar Noble. Soft agar culture was maintained in 5% $O_2$ and 5% $CO_2$, and was fed weekly with 1 mL per well with media containing 0.3% Difco Agar Noble. Colonies were stained overnight with 200 μL 0.2% p-Iodonitrotetrazolium chloride (Sigma, #18377A). A Pentax K20D with a macro lens (Sigma, 50 mm/f2.8 EX DG Macro) was used to take images of the colonies. NIH ImageJ software (ver 1.41) was used to count colony numbers.

HDAC Activity Assay

For HDAC activity assays, cells were harvested and sorted by flow cytometry as described above, washed 3 times with cold HBSS buffer, suspended in cold lysis buffer, and centrifuged at 4° C. Cell lysate supernatant was stored at 80° C. until use. The same amount of protein was loaded for the HDAC activity assay (Cayman Chemical Co., #10011563), according to the manufacturer's instructions. Resulting data were displayed as fluorescence units.

Statistical Analysis

T-tests were used to compare cell proliferation, sphere formations, and HDAC activities. Statistical analyses were performed using commercial software (GraphPad Prism 5.0, GraphPad Software Inc.) with significance at $p<0.05$.

What is claimed is:

1. A method for inhibiting the proliferation of or eliminating one or more epithelial carcinoma tumor stem cells that express HDAC1 and/or HDAC7 comprising contacting said one or more cells with an effective amount of at least one inhibitor of HDAC1 and/or an effective amount of at least one inhibitor of HDAC7, wherein an epithelial carcinoma tumor stem cell sample obtained from a source of said one or more cells has been determined to have an increased level or activity of HDAC1 protein and/or an increased level or activity of HDAC7 protein as compared to a standard level.

2. The method of claim 1 wherein the inhibitor specifically inhibits the level and/or activity of HDAC1 protein.

3. The method of claim 1 wherein the inhibitor specifically inhibits the level and/or activity of HDAC7 protein.

4. The method of claim 3 wherein the HDAC7 protein is phosphorylated.

5. The method of claim 1 comprising contacting said one or more cells with an effective amount of both at least one HDAC1 inhibitor and at least one HDAC7 inhibitor.

6. A method for treating a tumor comprising epithelial carcinoma tumor stem cells that express HDAC1 and/or HDAC7, the method comprising: administering to an individual in need of treatment for said tumor an effective amount of an agent which specifically inhibits the level and/or activity of HDAC1 and/or HDAC7 protein, wherein an epithelial carcinoma tumor stem cell sample obtained from said tumor has been determined to have an increased level or activity of HDAC1 protein and/or an increased level or activity of HDAC7 protein as compared to a standard level.

7. The method of claim 6 wherein the agent specifically inhibits the level and/or activity of a phosphorylated HDAC7 protein.

8. The method of claim 1, wherein the tumor stem cells comprise cells that have an increased level or activity of HDAC1 protein and/or an increased level or activity of HDAC7 protein as compared to a standard level.

9. The method of claim 1, wherein the method comprises detecting an increased level or activity of HDAC1 protein and/or an increased level or activity of HDAC7 protein in a sample obtained from a source of said one or more tumor stem cells, thereby detecting one or more tumor stem cells in said sample and then contacting said one or more tumor stem cells with an effective amount of at least one inhibitor of HDAC1 and/or an effective amount of at least one inhibitor of HDAC7.

10. The method of claim 1, wherein the at least one inhibitor of HDAC7 specifically inhibits the level or activity of a kinase that phosphorylates HDAC7 or specifically increases the level or activity of a phosphatase that dephosphorylates HDAC7.

11. The method of claim 1, comprising (i) identifying a candidate agent that reduces HDAC1 and/or HDAC7 expression, protein level, or activity; and (ii) contacting said one or more tumor stem cells with an effective amount of said candidate agent.

12. The method of claim 11, wherein identifying a candidate agent that reduces HDAC1 and/or HDAC7 expression, protein level, or activity comprises: (a) contacting HDAC1 and/or HDAC7 with a test substance; (b) measuring the level or activity of HDAC1 and/or HDAC7; and (c) determining that the test substance reduces the level or activity of HDAC1 and/or HDAC7, thereby identifying a candidate agent that reduces HDAC1 and/or HDAC7 protein level or activity.

13. The method of claim 11, wherein identifying a candidate agent that reduces HDAC1 and/or HDAC7 expression, protein level, or activity comprises: (a) expressing HDAC1 and/or HDAC7 protein in a cell population; (b) contacting said population with a candidate agent; (c) measuring the level of expression or activity of HDAC1 and/or HDAC7; wherein a decrease in expression or activity of the HDAC1 and/or HDAC7 protein relative to a control cell population not exposed to said candidate agent is indicative of HDAC1 and/or HDAC7 inhibitory activity of said candidate agent; and (d)

determining that the candidate agent reduces the level or activity of HDAC1 and/or HDAC7, thereby identifying a candidate agent that reduces HDAC1 and/or HDAC7 expression or activity.

14. The method of claim 11, wherein step (i) comprises identifying a candidate agent that specifically reduces HDAC1 and/or HDAC7 expression, protein level or activity, and/or HDAC7 protein phosphorylation.

15. The method of claim 6, wherein the tumor comprises cells that have an increased level or activity of HDAC1 protein and/or an increased level or activity of HDAC7 protein as compared to a standard level.

16. The method of claim 6, wherein the method comprises detecting one or more tumor stem cells and/or detecting an increased level or activity of HDAC1 protein and/or an increased level or activity of HDAC7 protein in a sample from said tumor as compared to a standard level and then administering an effective amount of an agent which specifically inhibits the level and/or activity of HDAC1 and/or HDAC7 protein to the individual.

17. A method comprising contacting one or more ovarian epithelial carcinoma tumor stem cells that express higher levels of (i) HDAC1 protein and/or (ii) HDAC7 protein, and/or (iii) phosphorylated HDAC7 protein compared to non-stem tumor cells in the tumor cell population from which the one or more ovarian epithelial carcinoma tumor stem cells are obtained with an effective amount of at least one inhibitor of HDAC1 and/or an effective amount of at least one inhibitor of HDAC7, wherein the level of HDAC1 protein and/or HDAC7 protein and/or phosphorylated HDAC7 protein in the one or more ovarian epithelial carcinoma tumor stem cells is decreased, thereby inhibiting the proliferation of or eliminating the one or more ovarian epithelial carcinoma tumor stem cells.

18. A method comprising contacting one or more breast epithelial carcinoma tumor stem cells that express higher levels of (i) HDAC1 protein and/or (ii) HDAC7 protein, and/or (iii) phosphorylated HDAC7 protein compared to non-stem tumor cells in the tumor cell population from which the one or more breast epithelial carcinoma tumor stem cells are obtained with an effective amount of at least one inhibitor of HDAC1 and/or an effective amount of at least one inhibitor of HDAC7, wherein the level of HDAC1 protein and/or HDAC7 protein and/or phosphorylated HDAC7 protein in the one or more breast epithelial carcinoma tumor stem cells is decreased, thereby inhibiting the proliferation of or eliminating the one or more breast epithelial carcinoma tumor stem cells.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial
<220> FEATURE:
<223> OTHER INFORMATION: short hairpin RNA vector

<400> SEQUENCE: 1
cttctcgtga gctaaagaa                                                   19

<210> SEQ ID NO 2
<211> LENGTH: 19
<212> TYPE: DNA
<213> ORGANISM: Artificial
<220> FEATURE:
<223> OTHER INFORMATION: short hairpin RNA vector

<400> SEQUENCE: 2
ccagcaagat cctcattgt                                                   19

<210> SEQ ID NO 3
<211> LENGTH: 19
<212> TYPE: DNA
<213> ORGANISM: Artificial
<220> FEATURE:
<223> OTHER INFORMATION: short hairpin RNA vector

<400> SEQUENCE: 3
gctaccatgt ttctgccaa                                                   19

<210> SEQ ID NO 4
<211> LENGTH: 19
<212> TYPE: DNA
<213> ORGANISM: Artificial
<220> FEATURE:
<223> OTHER INFORMATION: short hairpin RNA vector

<400> SEQUENCE: 4
ctaccatgtt tctgccaaa                                                   19

<210> SEQ ID NO 5
<211> LENGTH: 21
<212> TYPE: DNA
<213> ORGANISM: Artificial
<220> FEATURE:
<223> OTHER INFORMATION: short hairpin RNA vector

<400> SEQUENCE: 5
cggttaggtt gcttcaatct a                                                21

<210> SEQ ID NO 6
<211> LENGTH: 21
<212> TYPE: DNA
```

```
<213> ORGANISM: Artificial
<220> FEATURE:
<223> OTHER INFORMATION: short hairpin RNA vector

<400> SEQUENCE: 6
cctaatgagc ttccatacaa t                                              21

<210> SEQ ID NO 7
<211> LENGTH: 21
<212> TYPE: DNA
<213> ORGANISM: Artificial
<220> FEATURE:
<223> OTHER INFORMATION: short hairpin RNA vector

<400> SEQUENCE: 7
ccacagcgat gactacatta a                                              21

<210> SEQ ID NO 8
<211> LENGTH: 25
<212> TYPE: DNA
<213> ORGANISM: Artificial
<220> FEATURE:
<223> OTHER INFORMATION: short hairpin RNA vector

<400> SEQUENCE: 8
ccgggcaacc ataagacaaa ctcct                                          25
```